US007067481B2

(12) United States Patent
Fatheree et al.

(10) Patent No.: US 7,067,481 B2
(45) Date of Patent: Jun. 27, 2006

(54) CROSS-LINKED GLYCOPEPTIDE-CEPHALOSPORIN ANTIBIOTICS

(75) Inventors: Paul R. Fatheree, San Francisco, CA (US); Martin S. Linsell, San Mateo, CA (US); Daniel Marquess, Half Moon Bay, CA (US); Daniel D. Long, San Francisco, CA (US); Jason P. Chinn, Riverside, CA (US); Matthew B. Nodwell, Vancouver (CA); Edmund J. Moran, San Francisco, CA (US); James B. Aggen, Burlingame, CA (US)

(73) Assignee: Theravance, Inc., South San Francisco, CA (US)

( * ) Notice: Subject to any disclaimer, the term of this patent is extended or adjusted under 35 U.S.C. 154(b) by 69 days.

(21) Appl. No.: 10/851,428

(22) Filed: May 21, 2004

(65) Prior Publication Data

US 2004/0266666 A1    Dec. 30, 2004

Related U.S. Application Data

(60) Provisional application No. 60/473,065, filed on May 23, 2003.

(51) Int. Cl.
    *A61K 38/16* (2006.01)
(52) U.S. Cl. .......................................................... 514/8
(58) Field of Classification Search ...................... 514/8
    See application file for complete search history.

(56) References Cited

U.S. PATENT DOCUMENTS

| 4,220,761 A | 9/1980 | Takaya et al. |
| 4,341,775 A | 7/1982 | Takaya et al. |
| 4,366,153 A | 12/1982 | Takaya et al. |
| 4,487,767 A | 12/1984 | Takaya et al. |
| 4,921,851 A | 5/1990 | Kishimoto et al. |
| 4,943,567 A | 7/1990 | Nishizawa et al. |
| 5,693,791 A | 12/1997 | Truett et al. |
| 6,392,012 B1 | 5/2002 | Judice et al. |
| 6,437,119 B1 | 8/2002 | Truett |
| 6,444,786 B1 | 9/2002 | Judice et al. |
| 6,455,669 B1 | 9/2002 | Judice et al. |
| 6,518,242 B1 | 2/2003 | Chen et al. |
| 6,878,686 B1* | 4/2005 | Marquess et al. ............... 514/8 |
| 2003/0130173 A1 | 7/2003 | Fatheree et al. |
| 2004/0033939 A1 | 2/2004 | Marquess et al. |
| 2005/0026818 A1 | 2/2005 | Fatheree et al. |

FOREIGN PATENT DOCUMENTS

| GB | 2 033 377 A | 5/1980 |
| JP | 60-41682 | 3/1985 |
| WO | WO 99/42476 | 8/1999 |
| WO | WO 99/64049 A1 | 12/1999 |
| WO | WO 00/39156 | 7/2000 |
| WO | WO 03/031449 A2 | 4/2003 |
| WO | WO 03/099858 A1 | 12/2003 |

OTHER PUBLICATIONS

U.S. Appl. No. 09/457,926, filed Dec. 8, 1999, Christensen et al.
Boechkh et al., "Pharmacokinetics and Serum Bactericidal Activity of Vancomycin Alone and in Combination with Ceftazidime in Healthy Volunteers", Antimicrobial Agents and Chemotherapy, vol. 32. No. 1, pp. 95-95 (1988).
Bryskier, "Cephems:Fifty Years of Continuous Research", The Journal of Antibiotics, vol. 53, No. 10, pp. 1028-1037 (2000).
Bryskier, "Novelties in the field of parenteral cephem antibacterials since 1993", Exp. Opin. Invest. Drugs, 6(3), pp. 305-320 (1997).
Hammes, "Biosynthesis of Peptidoglycan in *Gaffkya homari*. The mode of action of Penicillin G and Mecillinam", Eur. J. Biochem., 70, pp. 107-113 (1976).
Hammes, "Biosynthesis of peptidoglycan in *Gaffkya homari*. The mode of action of penicillin G and mecillinam", Chemical Abstracts, vol. 86, No. 5, Abstract No. 26406 (1977).
Kim et al., "Synthesis and Antibacterial Activity of Cephalosporins Having Hydroxamic Acid at C-7 Position" Biorganic & Med. Chem. Letters. vol. 6, No. 17, pp. 2077-2080 (1996).
Kim et al., "Patents on β-lactam antibacterials: Jan. 1999 to Mar. 2001", Expert Opin. Ther. Patents, 11(8), pp. 1267-1276 (2001).
Lattrell et al., "Synthesis and Structure-Activity Relationships in the Cefpirome Series." Journal of Antibiotics. vol. XLI, No. 10, pp. 1374-1394 (1988).
Nicolaou et al., "Chemistry, Biology, and Medicine of the Glycopeptide Antibiotics", Angew. Chem. Intl. Ed., 38, pp. 2096-2152 (1999).
Pavlov et al., "A New Type of Chemical Modification of Glycopeptides Antibiotics: Aminomethylated Derivatives of Eremomycin and Their Antibacterial Activity", The Journal of Antibiotics, vol. 50, No. 6, pp. 509-513 (1997).
Pavlov et al., "Chemical Modification of Glycopeptide Antibiotics [VC1]", Russian Journal of Bioorganic Chemistry, vol. 24, No. 9, pp. 570-587 (1998).
Rao et al., "Tight Binding of a Dimeric Derivative of Vancoymycin with Dimeric L-Lys-D-Ala-D-Ala", J. Am. Chem. Soc. vol. 119, pp. 10286-10290 (1997).

(Continued)

*Primary Examiner*—Bruce R. Campell
*Assistant Examiner*—Thomas S. Heard
(74) *Attorney, Agent, or Firm*—Jeffrey A. Hagenah

(57) ABSTRACT

This invention provides cross-linked glycopeptide—cephalosporin compounds and pharmaceutically acceptable salts thereof which are useful as antibiotics. This invention also provides pharmaceutical compositions containing such compounds; methods for treating bacterial infections in a mammal using such compounds; and processes and intermediates useful for preparing such compounds.

35 Claims, 10 Drawing Sheets

OTHER PUBLICATIONS

Renoud-Grappin et al., "Imidazo[1,5-b]pyridazine-d4T conjugates:synthesis and anti-human immunodeficiency virus evaluation", Antiviral Chemistry & Chemotherapy, vol. 9, pp. 205-223 (1998).

Staroske et al., "Synthesis of Covalent Head-to-Tail Dimers of Vancomycin", Tetrahedron Letters 39, pp. 4917-4920 (1998).

Sundram et al., "General and Efficient Method for the Solution- and Solid-Phase Synthesis of Vancomycin Carboxamide Derivatives", J. Org. Chem., vol. 60, pp. 1102-1103 (1995).

Sundram et al., "Novel Vancomycin Dimers with Activity against Vancomycin-Resistant Enterococci", J. Am. Chem. Soc., vol. 118, pp. 13107-13108 (1996).

* cited by examiner

CROSS-LINKED GLYCOPEPTIDE-CEPHALOSPORIN ANTIBIOTICS

CROSS-REFERENCE TO RELATED APPLICATIONS

This application claims the benefit of U.S. Provisional Application No. 60/473,065, filed on May 23, 2003; the entire disclosure of which is incorporated herein by reference in its entirety.

BACKGROUND OF THE INVENTION

1. Field of the Invention

This invention is directed to novel cross-linked vancomycin—cephalosporin compounds which are useful as antibiotics. This invention is also directed to pharmaceutical compositions comprising such compounds; methods of using such compounds as antibacterial agents; and processes and intermediates for preparing such compounds.

2. State of the Art

Various classes of antibiotic compounds are known in the art including, for example, β-lactam antibiotics, such as cephalosporins, and glycopeptide antibiotics, such as vancomycin. Cross-linked antibiotic compounds are also known in the art. See, for example, U.S. Pat. No. 5,693,791, issued to W. L. Truett and entitled "Antibiotics and Process for Preparation"; WO 99/64049 A1, published on Dec. 16, 1999, and entitled "Novel Antibacterial Agents". Additionally, WO 03/031449 A2, published on Apr. 17, 2003, and entitled "Cross-Linked Glycopeptide—Cephalosporin Antibiotics" discloses compounds having a glycopeptide group covalently linked to the oxime moiety of a cephalosporin group.

Due to the potential for bacteria to develop resistance to antibiotics, however, a need exists for new antibiotics having unique chemical structures. Additionally, a need exists for novel antibiotics having improved antibacterial properties including, by way of example, increased potency against Gram-positive bacteria. In particular, a need exists for new antibiotics that are highly effective against antibiotic-resistant strains of bacteria, such as methicillin-resistant *Staphylococci aureus* (MRSA).

SUMMARY OF THE INVENTION

The present invention provides novel cross-linked glycopeptide—cephalosporin compounds that are useful as antibiotics. The compounds of this invention have a unique chemical structure in which a glycopeptide group is covalently linked to a pyridinium moiety of a cephalosporin group. Among other properties, compounds of this invention have been found to possess surprising and unexpected potency against Gram-positive bacteria including methicillin-resistant *Staphylococci aureus* (MRSA).

Accordingly, in one aspect, this invention provides a compound of formula I:

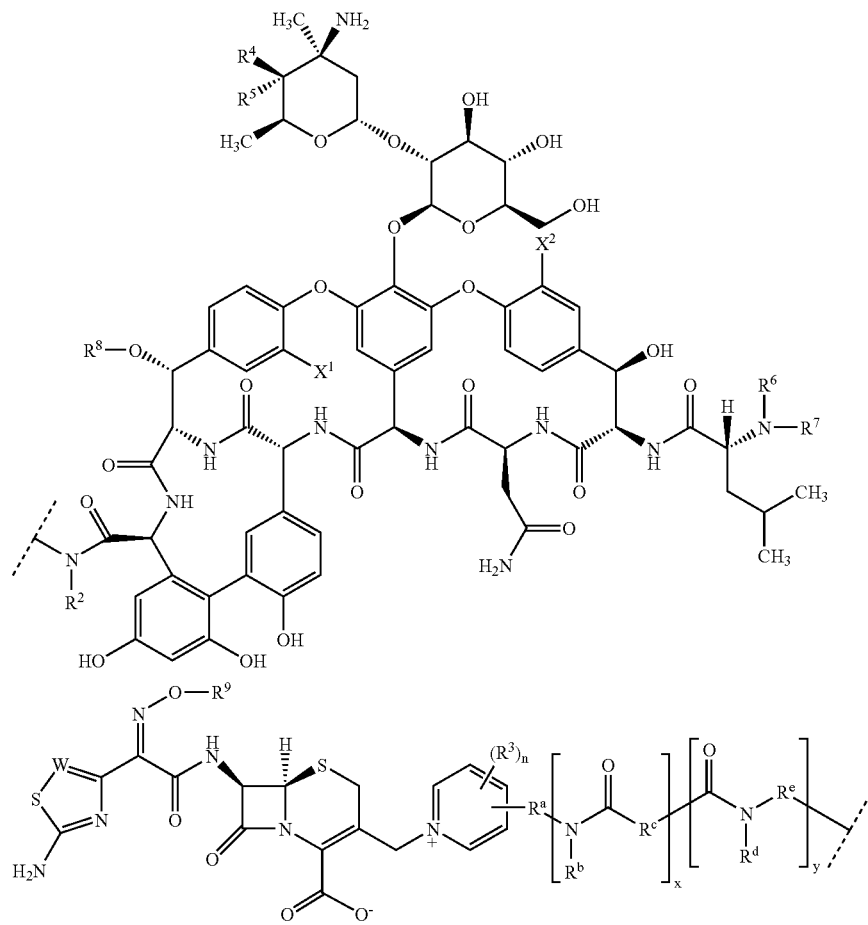

or a pharmaceutically acceptable salt thereof, wherein
each of $X^1$ and $X^2$ is independently hydrogen or chloro;
W is selected from the group consisting of N and CCl;
$R^2$ is hydrogen or $C_{1-6}$ alkyl;
one of $R^4$ and $R^5$ is hydroxy and the other is hydrogen;
each of $R^6$ and $R^7$ is independently hydrogen or methyl;
$R^8$ is hydrogen or a group of the formula:

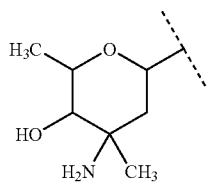

$R^9$ is selected from hydrogen, $C_{1-6}$ alkyl, and $C_{3-6}$ cycloalkyl, where alkyl and cycloalkyl may be substituted with —COOH or 1 to 3 fluorine atoms;

each $R^3$ is independently selected from $C_{1-6}$ alkyl, —OR, halo, —SR, —S(O)R, —S(O)$_2$R, and —S(O)$_2$OR, where —OC(O)R', —C(O)OR', —NHC(O)R', —C(O)N(R')$_2$, —CF$_3$, and —OCF$_3$, and side chains of naturally occurring amino acids, where each R' is independently hydrogen or $C_{1-4}$ alkyl; and R contains at most 20 non-hydrogen atoms;

Y, which links R" to the pyridinium ring at a meta or para position, is selected from a direct bond, NR', O (ether), S (sulfide), C(O) (carbonyl), NR'(CO), and (CO)NR', precluding direct bonds between heteroatoms in Y and R";

each $R^b$ and $R^d$ is independently selected from the group consisting of hydrogen, $C_{1-6}$ alkyl, $C_{2-6}$ alkenyl, and $C_{2-6}$ alkynyl;

each $R^c$ is independently —Y'—R"—Y'—, where each Y' is independently selected from the group consisting of a direct bond, O (ether), and NR', precluding direct bonds between heteroatoms in Y' and R"; and each $R^e$ is independently selected from the group defined by R" above.

In another aspect, the invention provides a compound of formula II:

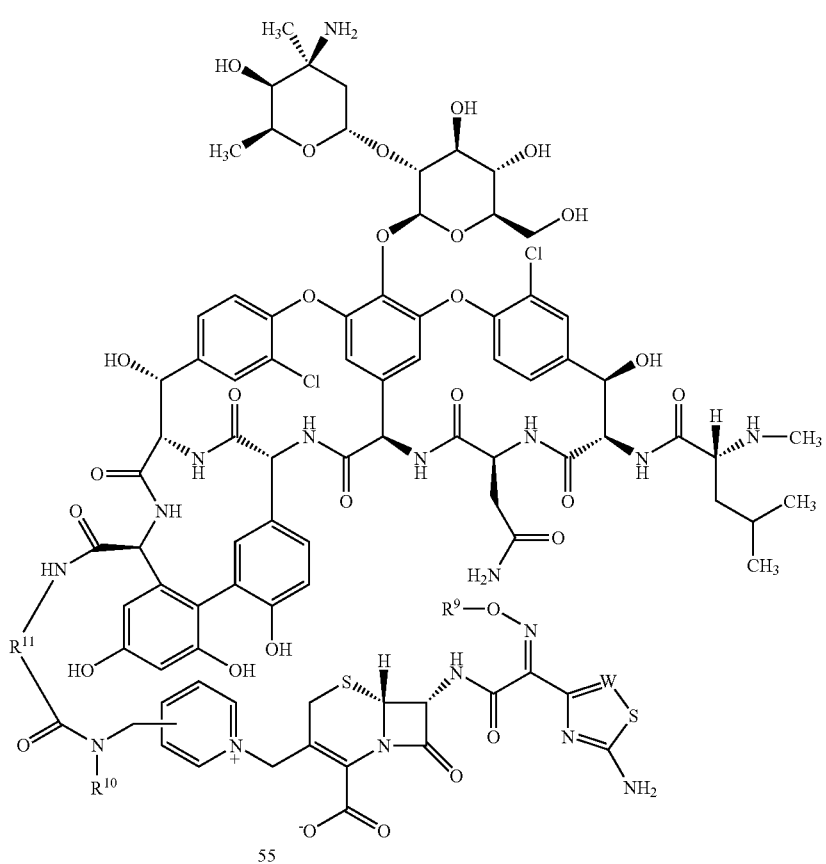

each R is independently $C_{1-6}$ alkyl, which may be substituted with COOH or 1 to 3 fluorine atoms;
n is 0, 1, 2 or 3;
x is 0, 1 or 2;
y is 0, 1 or 2;
$R^a$ is —Y—R"—, where
R" is selected from $C_{1-12}$ alkylene, $C_{2-12}$ alkenylene, $C_{2-12}$ alkynylene, $C_{3-6}$ cycloalkylene, $C_{6-10}$ arylene, $C_{2-9}$ heteroarylene, $C_{3-6}$ heterocycle, and combinations thereof, and is optionally substituted with 1 or 2 groups selected from Z, where Z consists of —OR', —SR', —F, —Cl, —N(R')$_2$, or a pharmaceutically acceptable salt thereof; wherein
W is selected from the group consisting of N and CCl;
$R^9$ is selected from hydrogen, $C_{1-6}$ alkyl, and $C_{3-6}$ cycloalkyl, where alkyl and cycloalkyl may be substituted with —COOH or 1 to 3 fluorine atoms;
the pyridinium ring has meta or para substitution;
$R^{10}$ is hydrogen or $C_{1-6}$ alkyl; and
$R^{11}$ is $C_{1-12}$ alkylene.

In another of its composition aspects, this invention provides a pharmaceutical composition comprising a pharmaceutically acceptable carrier and a therapeutically effective amount of a compound of formula I or formula II, or a pharmaceutically acceptable salt thereof, including any of the particular embodiments discussed herein.

Also provided are methods of inhibiting the growth of bacteria and/or inhibiting bacterial cell wall biosynthesis, by contacting bacteria with a growth-inhibiting amount of a compound of formula I or formula II, or a pharmaceutically acceptable salt thereof, including any of the particular embodiments discussed herein. In particular, the methods include those embodiments in which the compound is selected from the group consisting of those designated herein as Ia, Ib, Ic, Id, Ie, and If.

In a related aspect, the invention provides a method of treating a bacterial infection in a mammal, the method comprising administering to a mammal a pharmaceutical composition comprising a pharmaceutically acceptable carrier and a therapeutically effective amount of a compound of formula I or II, or a pharmaceutically acceptable salt thereof, including any of the particular embodiments discussed herein.

This invention is also directed to processes for preparing compounds of formula I or II or a salt thereof. Accordingly, in another of its method aspects, this invention provides a process for preparing a compound of formula I or a salt thereof; the process comprising reacting a compound of formula 1 or a salt, activated derivative, or protected derivative thereof, with a compound of formula 3 or 4 or a salt, activated derivative, or protected derivative thereof; to provide a compound of formula I or a salt thereof; wherein the compounds of formula 1, 3 and 4 are as defined herein.

Additionally, in another of its method aspects, this invention provides a process for preparing a compound of formula I or a salt thereof; the process comprising reacting a compound of formula 2 or a salt, activated derivative, or protected derivative thereof; with a compound of formula 5 or a salt, activated derivative, or protected derivative thereof; to provide a compound of formula I or a salt thereof; wherein the compounds of formula 2 and 5 are as defined herein.

In one embodiment, these processes further comprise the step of forming a pharmaceutically acceptable salt of a compound of formula I. This invention is also directed to the product prepared by any of these processes.

This invention is also directed to a compound of formula I or II, or a pharmaceutically acceptable salt thereof, for use in therapy. Additionally, this invention is directed to the use of a compound of formula I or II, or a pharmaceutically acceptable salt thereof, for the manufacture of a medicament, including a medicament for treating a bacterial infection in a mammal.

DETAILED DESCRIPTION OF THE INVENTION

Figure 1:
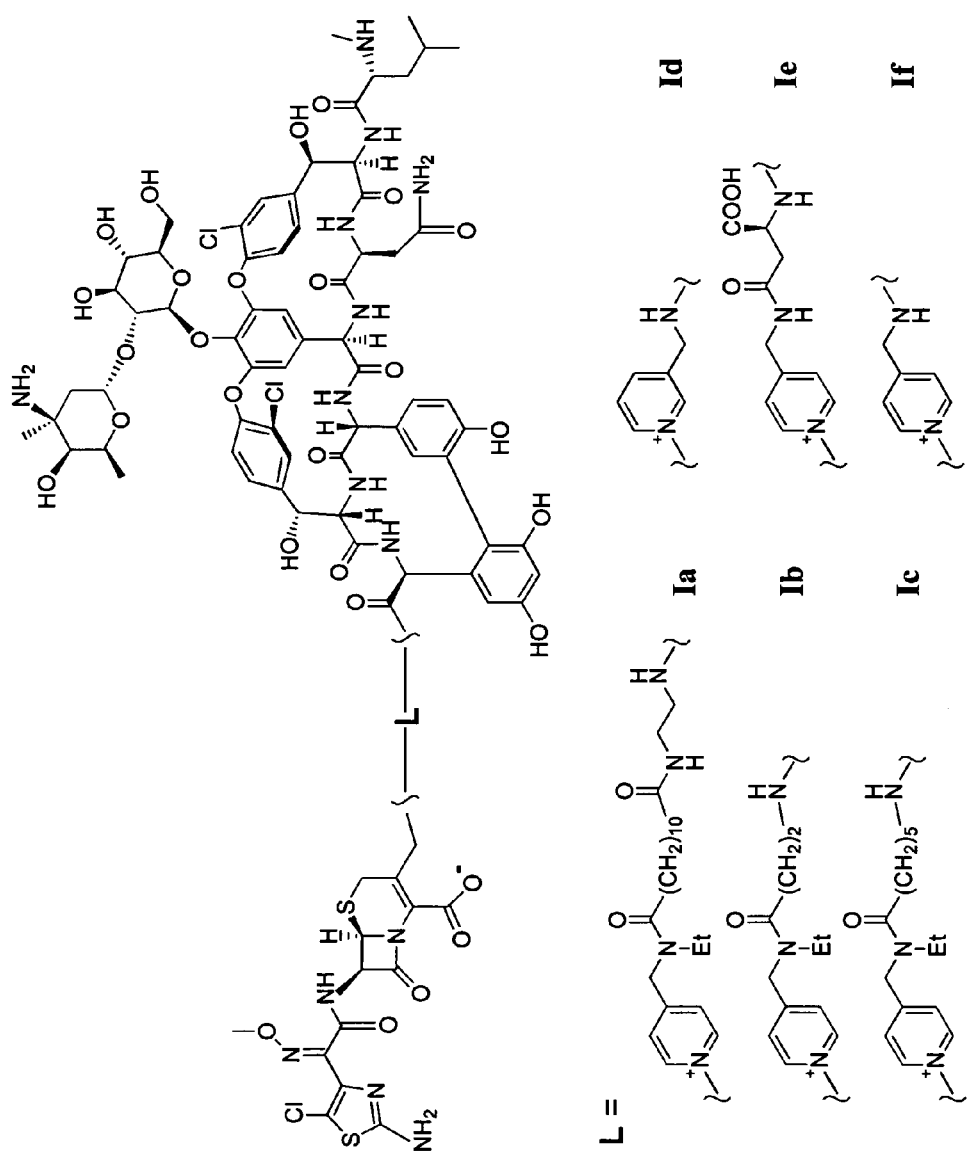
FIG. 1 shows examples of cross-linked glycopeptide-cephalosporin antibiotics, in accordance with selected embodiments of the invention.

This invention provides novel glycopeptide—cephalosporin compounds of formula I or II, or pharmaceutically acceptable salts thereof. These compounds have multiple chiral centers and, in this regard, the compounds are intended to have the stereochemistry shown. In particular, the glycopeptide portion of the compound is intended to have the stereochemistry of the corresponding naturally-occurring glycopeptide (i.e., vancomycin, chloroorienticin A and the like). The cephalosporin portion of the molecule is intended to have the stereochemistry of known cephalosporin compounds. However, it will be understood by those skilled in the art that minor amounts of isomers having a different stereochemistry from that shown may be present in the compositions of this invention provided that the utility of the composition as a whole is not significantly diminished by the presence of such isomers.

Additionally, the linking portion of the compounds of this invention may contain one or more chiral centers. Typically, this portion of the molecule will be prepared as a racemic mixture. If desired, however, pure stereoisomers (i.e., individual enantiomers or diastereomers) may be used or a stereoisomer-enriched mixture can be employed. All such stereoisomers and enriched mixtures are included within the scope of this invention.

In addition, compounds of this invention contain several acidic groups (i.e., carboxylic acid groups) and several basic groups (i.e., primary and secondary amine groups) and therefore, the compounds of formula I can exist in various salt forms. All such salt forms are included within the scope of this invention. Also, since the compounds of formula I contain a pyridinium ring, an anionic counterion for the pyridinium group may optionally be present including, but not limited to, halides, such as chloride; carboxylates, such as acetate; and the like.

Definitions

The following terms, as used herein, have the following meanings, unless otherwise indicated:

The term "alkyl" refers to a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" refers to a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkenyl" refers to a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like.

The term "alkynyl" refers to a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like.

The term "aryl" refers to a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "arylene" refers to a divalent aromatic hydrocarbon having a single ring (i.e., phenylene) or fused rings (i.e., naphthalenediyl). Unless otherwise defined, such arylene groups typically contain from 6 to 10 carbon ring atoms. Representative arylene groups include, by way of example, 1,2-phenylene, 1,3-phenylene, 1,4-phenylene, naphthalene-1,5-diyl, naphthalene-2,7-diyl, and the like.

The term "cycloalkyl" refers to a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like.

The term "cycloalkylene" refers to a divalent saturated carbocyclic hydrocarbon group. Unless otherwise defined, such cycloalkylene groups typically contain from 3 to 10 carbon atoms. Representative cycloalkylene groups include, by way of example, cyclopropane-1,2-diyl, cyclobutyl-1,2-diyl, cyclobutyl-1,3-diyl, cyclopentyl-1,2-diyl, cyclopentyl-1,3-diyl, cyclohexyl-1,2-diyl, cyclohexyl-1,3-diyl, cyclohexyl-1,4-diyl, and the like.

The term "halo" refers to fluoro, chloro, bromo and iodo.

The term "heteroaryl" refers to a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heteroarylene" refers to a divalent aromatic group having a single ring or two fused rings and containing at least one heteroatom (typically 1 to 3 heteroatoms) selected from nitrogen, oxygen or sulfur in the ring. Unless otherwise defined, such heteroarylene groups typically contain from 5 to 10 total ring atoms. Representative heteroarylene groups include, by way of example, divalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heterocyclyl" or "heterocyclic" refers to a monovalent or divalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom.

The term "cephalosporin" is used herein in its art-recognized manner to refer to a β-lactam ring system having the following general formula and numbering system:

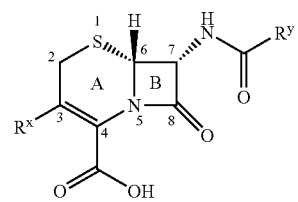

where $R^x$ and $R^y$ represent the remaining portion of the cephalosporin.

The term "glycopeptide antibiotic" or "glycopeptide" is used herein in its art-recognized manner to refer to the class of antibiotics known as glycopeptides or dalbahpeptides. See, for example, R. Nagarajan, "Glycopeptide Antibiotics", Marcel Dekker, Inc. (1994) and references cited therein. Representative glycopeptides include vancomycin, A82846A (eremomycin), A82846B (chloroorienticin A), A82846C, PA-42867-A (orienticin A), PA-42867-C, PA-42867-D and the like.

The term "vancomycin" is used herein in its art-recognized manner to refer to the glycopeptide antibiotic known as vancomycin. In the compounds of the present invention, the point of attachment for the linking moiety is at the "C-terminus" of vancomycin.

The term "cross-linked glycopeptide—cephalosporin antibiotics" refers to covalent conjugation of a glycopeptide component to a cephalosporin component.

The term "pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids. Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like. Particularly preferred are citric, hydrobromic, hydrochloric, maleic, phosphoric, sulfuric and tartaric acids.

The term "salt thereof" refers to a compound formed when the hydrogen of an acid is replaced by a cation, such as a metal cation or an organic cation and the like (e.g., an $NH_4^+$ cation and the like). Preferably, the salt is a pharmaceutically acceptable salt, although this is not required for salts of intermediate compounds which are not intended for administration to a patient.

The term "therapeutically effective amount" refers to an amount sufficient to effect treatment when administered to a patient in need of treatment.

The term "treating" or "treatment" as used herein refers to the treating or treatment of a disease or medical condition (such as a bacterial infection) in a patient, such as a mammal (particularly a human or a companion animal) which includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The term "growth-inhibiting amount" refers to an amount sufficient to inhibit the growth or reproduction of a microorganism or sufficient to cause death or lysis of the microorganism including gram-positive bacteria.

The term "cell wall biosynthesis-inhibiting amount" refers to an amount sufficient to inhibit cell wall biosynthesis in a microorganism including gram-positive bacteria.

The term "leaving group" refers to a functional group or atom which can be displaced by another functional group or atom in a substitution reaction, such as a nucleophilic substitution reaction. By way of example, representative leaving groups include chloro, bromo and iodo groups; and sulfonic ester groups, such as mesylate, tosylate, brosylate, nosylate and the like; activated ester groups, such as such as 7-azabenzotriazole-1-oxy and the like; acyloxy groups, such as acetoxy, trifluoroacetoxy and the like.

The term "protected derivatives thereof" refers to a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as ap-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, N.Y., 1999, and references cited therein.

The term "amino-protecting group" refers to a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term "carboxy-protecting group" refers to a protecting group suitable for preventing undesired reactions at an carboxy group. Representative carboxy-protecting groups include, but are not limited to, esters, such as methyl, ethyl, tert-butyl, benzyl (Bn), p-methoxybenzyl (PMB), 9-fluorenylmethyl (Fm), trimethylsilyl (TMS), tert-butyldimethylsilyl (TBS), diphenylmethyl (benzhydryl, DPM) and the like.

An "activated derivative", with respect to a carboxylic acid or protected derivative thereof, refers to the product, typically a reactive ester, resulting from reaction of the carboxylic acid or derivative with an activating (coupling) agent, such as, for example, 1-hydroxybenzotriazole (HOBT), 1-hydroxy-7-azabenzotriazole (HOAT), or others described below or otherwise known in the art.

A "side chain of a naturally occurring amino acid" refers to the group R in the formula $HOOC—CHR—NH_2$, where this formula represents an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, and preferably selected from alanine, arginine, asparagine, aspartic acid, cysteine, glutamine, glutamic acid, glycine, isoleucine, leucine, lysine, methionine, serine, threonine, and valine.

Representative Embodiments of Compounds of the Invention

The following substituents and values are intended to provide representative examples and embodiments of various aspects of this invention. These representative values are intended to further define such aspects and embodiments and are not intended to exclude other embodiments or limit the scope of this invention. In this regard, the representation that a particular value or substituent is preferred is not intended in any way to exclude other values or substituents from this invention unless specifically indicated.

In compounds of formula I, any heteroarylene or heterocyclic group present in R" preferably has 5 or 6, typically 6, total ring atoms, and each aryl group has 6 total ring atoms. The group R" is preferably an alkylene chain, and is preferably linear.

Each group $R^3$, when present, is preferably selected independently from unsubstituted $C_{1-4}$ alkyl, unsubstituted $C_{1-4}$ alkoxy, fluoro, and chloro. In one embodiment, n is 1 or 2, and each $R^3$ is independently selected form methyl, methoxy, fluoro, and chloro. In another embodiment, n is zero, such that no group $R^3$ is present.

In one preferred embodiment, $R^8$ is hydrogen. In another preferred embodiment, $R^8$ is a group of the formula:

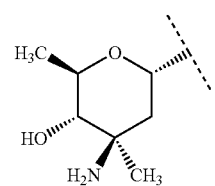

In selected embodiments, $R^9$ is hydrogen or $C_{1-4}$ alkyl, including hydrogen or methyl. In one embodiment $R^9$ is hydrogen. In another embodiment, $R^9$ is methyl.

In one embodiment, W is CCl. In another embodiment, W is N.

Selected embodiments of other variables of formula I include, independently of each other: for $X^1$ and $X^2$, chloro; for $R^2$, hydrogen or $C_{1-4}$ alkyl; for $R^4$ and $R^5$, hydroxyl and hydrogen, respectively; for $R^6$ and $R^7$, hydrogen and methyl, respectively; and for $R^8$, hydrogen.

In other selected embodiments, $R^a$ is —Y—R"—, where R" is $C_{1-6}$ alkylene, $C_{2-6}$ alkenylene, or $C_{2-6}$ alkynylene, and Y is selected from a direct bond, NR', O, S, C(O), NR'(CO), and (CO)NR', where R' is hydrogen or methyl. In one embodiment, Y is a direct bond. In further embodiments of the group $R^a$, R" is $C_{1-6}$ alkylene or, more preferably, $C_{1-4}$ alkylene, e.g. methylene, ethylene, propylene or butylene.

Preferably, in the group $R^a$, Y is a direct bond, and R" is $C_{1-6}$ alkylene or, more preferably, $C_{1-4}$ alkylene, e.g. methylene.

The pyridinium ring in formula I is typically meta or para substituted, more generally para substituted.

Preferably, the variable x is 0 or 1. When x is not 0, the group $R^b$ is preferably selected from the group consisting of hydrogen, $C_{1-4}$ alkyl or $C_{2-4}$ alkenyl. In one embodiment, $R^b$ is hydrogen or $C_{1-4}$ alkyl.

The group $R^c$, when x is not 0, is preferably —Y'—R"—Y'—, where each Y' is independently selected from a direct bond, O, and NR', where R' is hydrogen or methyl, and R" is selected from $C_{1-12}$ alkylene, $C_{2-12}$ alkenylene, and $C_{2-12}$ alkynylene, wherein the alkylene, alkenylene or alkynylene groups are optionally substituted with 1 or 2 groups selected from Z or the side chain of a naturally-occurring amino acid. Preferably, in the group $R^c$, each Y' is a direct bond, and R" is $C_{1-12}$ alkylene or $C_{2-12}$ alkenylene, which may be substituted with 1 or 2 groups selected from Z and a side chain of naturally-occurring amino acid. In another embodiment of the group $R^c$, R" is $C_{1-12}$ alkylene, including $C_{1-6}$ alkylene, and is unsubstituted or substituted with a —COOH group.

Preferably, the variable y is 0 or 1. When y is not 0, the group $R^d$ is preferably selected from the group consisting of hydrogen and $C_{1-4}$ alkyl, and, in selected embodiments, hydrogen and methyl. In one embodiment, $R^d$ is H. The group $R^e$, when y is not 0, is preferably selected from $C_{1-12}$ alkylene, $C_{2-12}$ alkenylene, and $C_{2-12}$ alkynylene. In one embodiment, $R^e$ is $C_{1-12}$ alkylene. More preferably, $R^e$ is selected from $C_{1-6}$ alkylene, $C_{2-6}$ alkenylene, and $C_{2-6}$ alkynylene, and most preferably from $C_{2-4}$ alkenylene and $C_{1-4}$ alkylene.

The group $R^2$, in selected embodiments, is hydrogen or $C_{1-4}$ alkyl. In further embodiments, $R^2$ is hydrogen or methyl; in one embodiment, $R^2$ is hydrogen.

In selected embodiments, x and y are independently selected from 0 and 1. Accordingly, preferred embodiments include compounds in which x+y=0, compounds in which x+y=1, and compounds in which x+y=2. Alternatively, preferred embodiments include compounds in which the "linker" structure, represented by "L" in FIG. 1, includes no more than about 30 carbon atoms, excluding the pyridinium ring.

An example of a compound of the invention in which x=y=1 is the compound designated herein as Ia. Examples of invention compounds in which x=1 and y=0 include those designated herein as Ib, Ic, and Ie. Examples of invention compounds in which x=y=0 include those designated herein as Id and If (see FIG. 1).

One exemplary class of compounds of structure I is that in which: x is 0 or 1; y is 0 or 1; $R^a$ is methylene; $R^b$ (when x is 1) is hydrogen, methyl, or ethyl; $R^c$ (when x is 1) is $C_{1-12}$ alkylene, preferably $C_{1-6}$ alkylene, e.g. ethylene or n-pentylene (—(CH$_2$)$_5$—), which may be substituted with —COOH; $R^d$ (when y is 1) is hydrogen; and $R^e$ (when y is 1) is ethylene (—CH$_2$CH$_2$—). Specific embodiments of this class of structure I include the compounds designated herein as Ia, Ib, Ic, Id, Ie, and If. In one embodiment of this class, x is 1; y is 0; $R^a$ is methylene; $R^b$ is hydrogen, methyl, or ethyl; and $R^c$ is $C_{2-6}$ alkylene, e.g. ethylene or n-pentylene (—(CH$_2$)$_5$—). Specific embodiments of this class of structure I include the compounds designated herein as Ib and Ic.

A subset of the invention compounds of formula I can also be defined by formula II. In selected embodiments of formula II, W is CCl. In other selected embodiments, $R^9$ is hydrogen or $C_{1-4}$ alkyl, including hydrogen or methyl.

$R^{10}$ is hydrogen or $C_{1-6}$ alkyl, preferably hydrogen or $C_{1-4}$ alkyl, including hydrogen, methyl or ethyl. In another embodiment, $R^{10}$ is ethyl.

In further selected embodiments, $R^{11}$ is $C_{1-10}$ alkylene, preferably $R^{11}$ is $C_{2-10}$ alkylene, and more preferably $C_{2-6}$ alkylene, e.g. —(CH$_2$)$_2$— or —(CH$_2$)$_5$—.

As for formula I above, the pyridinium ring in formula II is typically meta or para substituted, more generally para substituted.

Examples of invention compounds in accordance with formula II include those designated herein as Ib and Ic (see FIG. 1).

While not intending to be limited by theory, the compounds of formulas I and II are believed to inhibit bacterial cell wall biosynthesis, thereby inhibiting the growth of the bacteria or causing lysis of the bacteria. Accordingly, they are useful as antibiotics.

Among other properties, compounds of the invention have been found to possess surprising and unexpected potency against gram-positive bacteria, including methicillin-resistant *Staphylococci aureus* (MRSA) and methicillin-resistant *Staphylococci epidermitis* (MRSE), as described further below.

General Synthetic Procedures

The cross-linked glycopeptide—cephalosporin compounds of this invention can be prepared from readily available starting materials, preferably via the intermediate compounds 1–5 described herein. It will be appreciated that where typical or preferred process conditions (i.e., reaction temperatures, times, mole ratios of reactants, solvents, pressures, etc.) are given, other process conditions can also be used, as determined by one skilled in the art, unless otherwise stated. Optimum reaction conditions may vary with the particular reactants or solvent used, but such conditions can be readily determined by one skilled in the art by routine optimization procedures.

Additionally, as will be apparent to those skilled in the art, conventional protecting groups may be necessary or desired to prevent certain functional groups from undergoing undesired reactions. Suitable protecting groups for a particular functional group, as well as suitable conditions for protection and deprotection of such functional groups, are well known in the art. Protecting groups other than those illustrated in the procedures described herein may be used, if desired. For example, numerous protecting groups, and means for their introduction and removal, are described in T. W. Greene and G. M. Wuts, *Protecting Groups in Organic Synthesis*, Third Edition, Wiley, N.Y., 1999, and references cited therein.

In a preferred method of synthesis, the compounds of formula I, where y is 0, or, in selected embodiments, the compounds of formula II, are prepared by reacting a glycopeptide of formula 1:

In preparing compounds of formula II, variables in structures 1, 3, and/or 4 are defined as follows: n is 0; x is 1; y is 0; $R^a$ is $CH_2$; $R^b$ is hydrogen or $C_{1-6}$ alkyl (as defined for $R^{10}$ above); $R^c$ is $C_{1-12}$ alkylene (as defined for $R^{11}$ above);

1

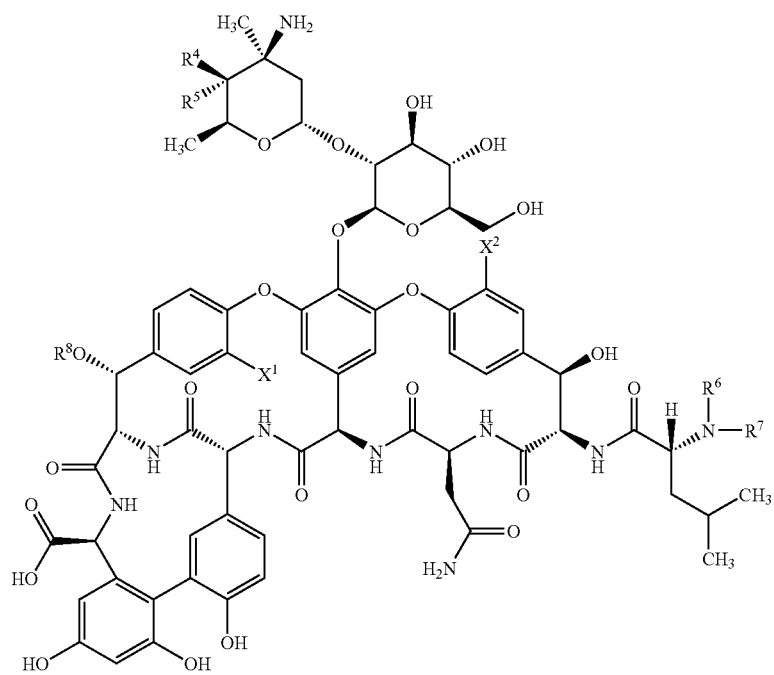

where $R^4$–$R^8$, $X^1$ and $X^2$ are as defined herein, or a salt, or an activated C-terminal carboxyl derivative and/or amine-protected derivative thereof, with a compound of formula 3 or 4:

$R^2$, $R^5$, and $R^6$ are hydrogen; $R^7$ is $CH_3$; $R^9$ is as defined herein; $R^4$ is OH; and $X^1$ and $X^2$ are Cl.

Typically, the reaction is conducted by coupling glycopeptide 1, or a salt thereof, with about 0.5 to about 1.5

3

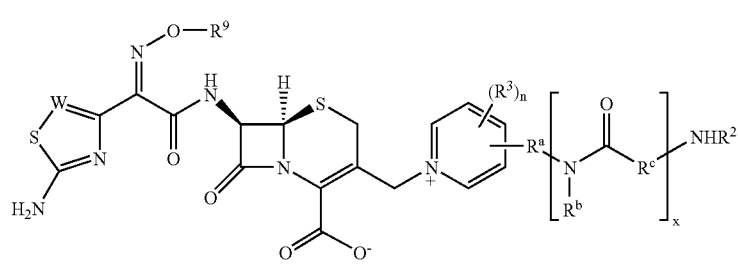

4

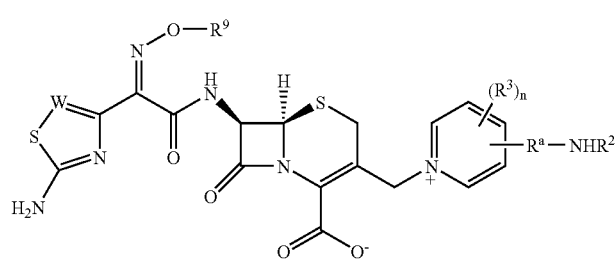

where W, $R^2$, $R^3$, $R^9$, $R^{a-e}$, n, x, and y are as defined herein, or a salt or carboxy-protected derivative thereof; to provide a compound of formula I or II, or a salt or protected derivative thereof. Preferred embodiments of 1, 3 and 4 are as described above.

equivalents, preferably about 0.9 to about 1.1 equivalents, of a compound of formula 3 or 4, in an inert diluent, such as DMF, using a conventional carboxylic acid—amine (peptide) coupling reagent, as discussed further below. In this reaction, glycopeptide 1, or a salt thereof, is typically first contacted with the coupling reagent in the presence of an excess, preferably about 1.8 to about 2.2 equivalents, of an amine, such as diisopropylethylamine at a temperature ranging from about −20° C. to about 25° C., preferably at ambient temperature, for about 0.25 to about 3 hours. Preferably, excess trifluoroacetic acid (typically about 2 equivalents) is then added to form a TFA salt of any excess diisopropylethylamine. The reaction is then generally cooled to a temperature of about −20° C. to about 10° C., preferably to about 0° C., and intermediate 3 or 4 is added, followed by excess 2,4,6-collidine. This reaction is typically maintained at about 0° C. for about 1 to about 6 hours, or until the reaction is substantially complete.

Alternatively, for preparing compounds of formula I where y is not 0, a glycopeptide derivative of formula 2, where $R^2$, $R^4$–$R^8$, $R^{d-e}$, $X^1$ and $X^2$ are as defined herein, or a salt or protected derivative thereof, can be reacted with intermediate of formula 5, where W, $R^3$, $R^9$, $R^{a-c}$, n and x, are as defined herein, or a salt or activated or protected derivative thereof. Preferred embodiments of 2 and 5 are as described above.

favored at the C-terminal primary amine. See, for example, the preparation of Ia illustrated in FIG. 3 and described further in Example 4.

For preparation of compounds of formula I in which y>1, a similar strategy can be followed, where one or more additions of an amino acid, e.g. of structure $HNR^d$—$R^e$—COOH, to the C-terminal —$NHR^d$ group of intermediate 2 precedes the reaction with intermediate 5.

Preferred coupling reagents, or activating reagents, for use in these reactions include benzotriazol-1-yloxy tripyrrolidinophosphonium hexafluorophosphate (PyBOP), preferably used in the amount of about 0.5 to 1.5 equivalents, preferably about 0.9 to 1.1 equivalents, in combination with about 0.5 to 1.5 equivalents, preferably about 0.9 to 1.1 equivalents, of 1-hydroxybenzotriazole (HOBT) or 1-hydroxy-7-azabenzotriazole (HOAT). Other suitable coupling reagents include O-(7-azabenzotriazol-1-yl)-N,N,N',N'-tetramethyluronium hexafluorophosphate (HATU); bis(2-oxo-3-oxazolidinyl)phosphinic chloride (BOP-Cl); diphenylphosphoryl azide (DPPA); diphenylphosphinic chloride; diphenyl chlorophosphate (DPCP) and HOAT; 1-(3-dim-

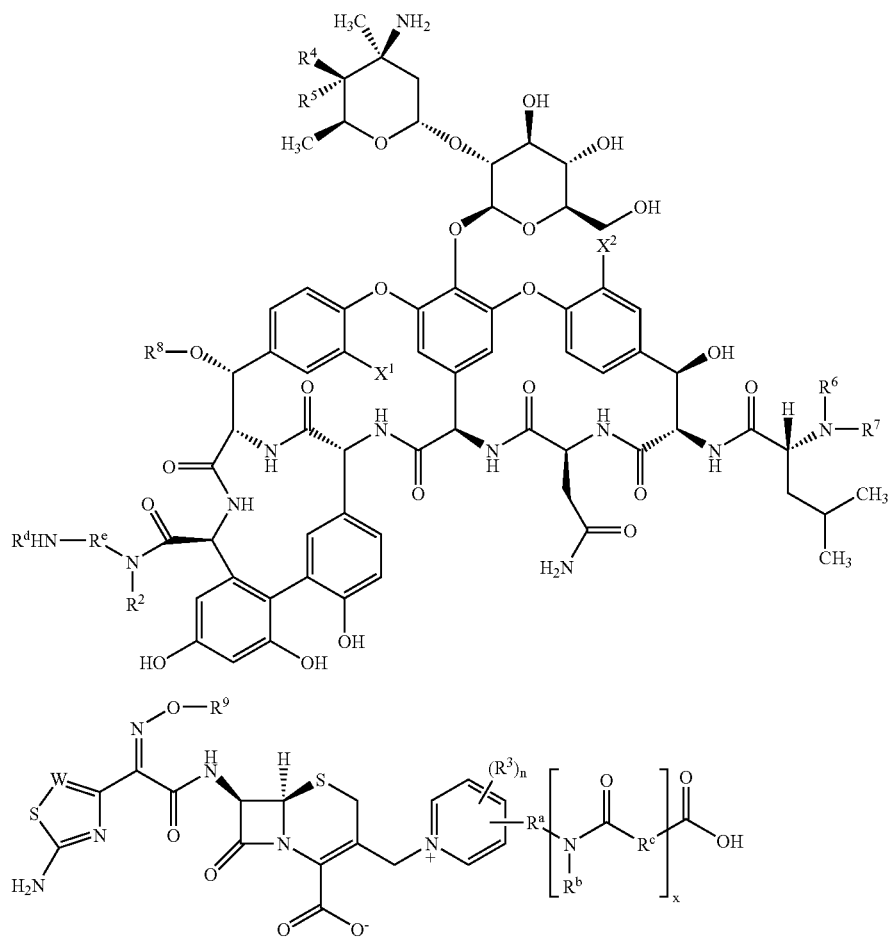

ethylaminopropyl)-3-ethylcarbodiimide hydrochloride (EDAC); pentafluorophenyl diphenylphosphinate, and the like.

After the coupling reaction is complete, any protecting groups present in the product are then removed using conventional procedures and reagents. For example, deprotection of N-trityl, N-BOC(N-tert-butoxycarbonyl) and/or COO-PMB (para-methoxybenzyl ester) can be effected by treatment with excess trifluoroacetic acid and excess anisole or triethylsilane in an inert diluent, such as dichloromethane or heptane, at ambient temperature for about 1 to about 12 hours, or until the reaction is complete. The deprotected product can be purified using conventional procedures, such as column chromatography, HPLC, recrystallization and the like.

Glycopeptides of formula 1 suitable for use in the above procedure are either commercially available or can be prepared by fermentation of the appropriate glycopeptide-producing organism, followed by isolation of the glycopeptide from the resulting fermentation broth using art recognized procedures and equipment. The derivative 2 is readily prepared by reaction of 1 with a diamine, as described, for example, in Example 3.

Figure 2:
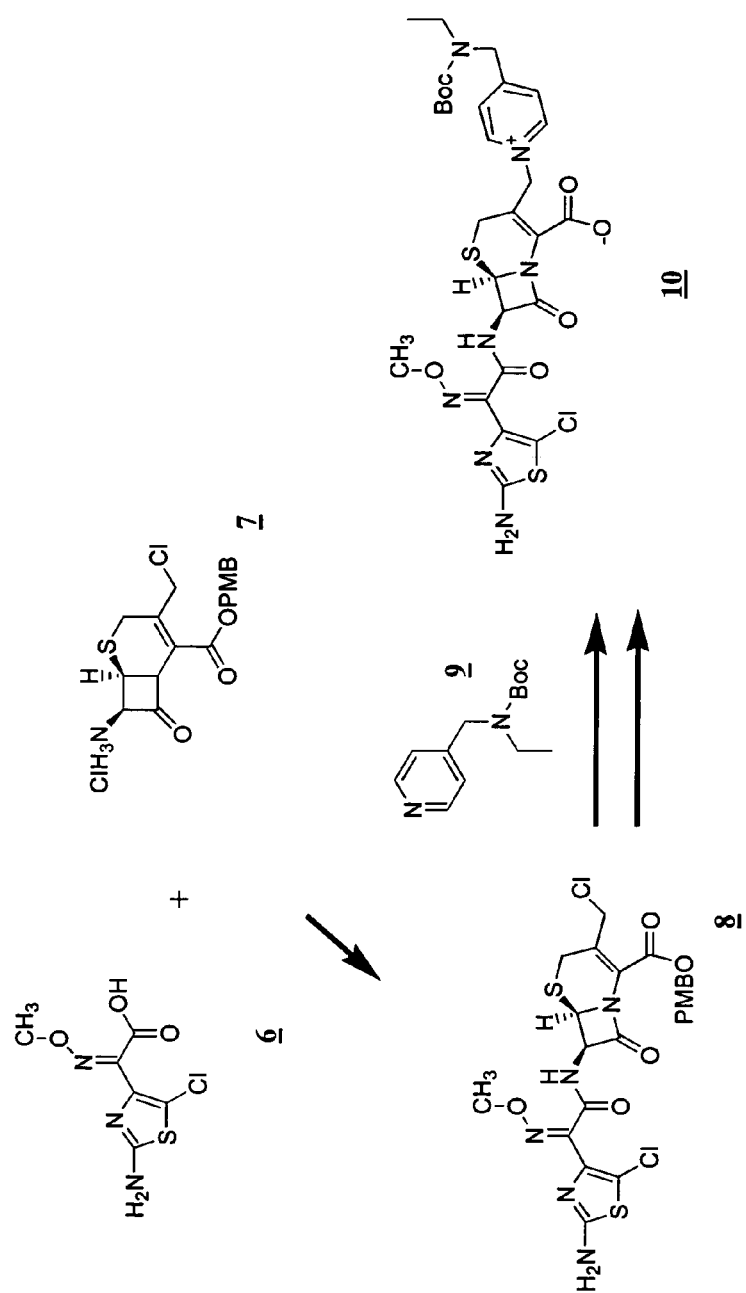
FIG. 2 shows a synthetic scheme for preparing cephalosporin intermediates that are useful for preparing cross-linked glycopeptide-cephalosporin antibiotics.

The cephalosporin intermediates 3 and 4 used in the above procedures are readily prepared from commercially available starting materials and reagents using conventional procedures. By way of example, an intermediate of formula 4 can be prepared as shown in FIG. 2 and described in Examples 1 and 2. Briefly, 2-amino-5-chloro-α-methoxy-imino-4-thiazole acetic acid (6) was reacted with the amino cephalosporinic ester 7, catalyzed with EDAC, forming an amide linkage. This product (8) was then treated with TFA and anisole to cleave the PMB ester, followed by displacement of the primary chloride with a pyridine derivative. The pyridine derivative contains substituents —$R^a$—$NHR^2$ and optionally substituent(s) $R^3$, as shown in structure 4 above. In the preparation shown in FIG. 2, the compound 4-(N-t-BOC-N-ethyl)aminomethylpyridine (9) is employed, such that $R^a$ is methylene and $R^2$ is ethyl. This reaction gives the intermediate (10) in protected form; deprotection with TFA gives the intermediate 4a (intermediate 4 where W is CCl, $R^9$ is Me, n is 0, $R^a$ is $CH_2$, and $R^2$ is Et).

In an alternate process, the product 8 was reacted with sodium iodide in acetone, followed by reaction with 9. Reaction with TFA/anisole then was used to remove both the Boc and PMB protecting groups.

Various substituted pyridines for use in the above reactions are either commercially available or can be prepared from commercially available starting materials and reagents using conventional procedures. For example, various aminoalkyl-substituted pyridines are commercially available, e.g. aminomethylpyridines, where $R^a$ is methylene, and aminoethyl pyridines, where $R^a$ is ethylene, or can be prepared using standard organic synthesis procedures. Representative substituted pyridine derivatives for use in this reaction include those in which $R^3$ is selected from methyl, methoxy, thiomethoxy, carboxythiomethoxy, fluoro, chloro, phenyl, cyclopropyl, carboxylic acid, carboxamide, and combinations thereof. For preparation of compounds in which Y, which links R" to the pyridinium ring, is selected from NR', O (ether), S (sulfide), C(O) (carbonyl), NR'(CO), and (CO)NR', starting pyridine compounds are commercially available or can be prepared by well known procedures. For example, 3-hydroxypyridine, 4-hydroxypyridine, 3-aminopyridine, 4-aminopyridine, 4-mercaptopyridine, nicotinic acid and isonicotinic acid are commercially available from Aldrich Chemical Co, Milwaukee, Wis.

Intermediate 4 can be further substituted to form intermediates of formula 3. For example, FIG. 4 shows reaction of an intermediate of formula 4 with N-(t-BOC)-β-alanine (see Example 5, preparation of Ib) and with aspartic acid (see Example 8, preparation of Ie) to form intermediates of formula 3, where x is 1, after deprotection. Further addition(s) of β-alanine or like compounds, such as other amino acids, could be employed to form intermediates of formula 3 in which x>1. Reaction of intermediate 4 with a diacid, e.g. of the structure HOOC—$R^c$—COOH, can be employed (with suitable activating and/or protecting reagents) to form intermediates of formula 5, in which x is 1 (see FIG. 3; Example 4; preparation of Ia). To form intermediates of formula 5 in which x>1, intermediate 4 would first be reacted with one or more moles of an amino acid (e.g. of the structure HOOC—$R^c$—$NHR^b$).

In preparing compounds in which, in the group $R^c$, Y' is selected from O (ether) and NR' (rather than a direct bond), linking moieties including $R^c$ will include one or more carbamate or urea linkages, rather than amide linkages. Such linkages can be formed by conventional methods. For example, an amine (such as —$NHR^2$ in intermediate 3 or 4) can be reacted with an isocyanate or a chloroformate to form, respectively, a urea or carbamate linkage.

Further details regarding specific reaction conditions and procedures for preparing representative compounds of this invention or intermediates thereto are described in the Examples set forth below.

Pharmaceutical Compositions

The cross-linked glycopeptide—cephalosporin compounds of this invention are typically administered to a patient in the form of a pharmaceutical composition. Accordingly, in one of its composition aspects, this invention is directed to a pharmaceutical composition comprising a pharmaceutically acceptable carrier or excipient and a therapeutically effective amount of a compound of formula I or II or a pharmaceutically acceptable salt thereof.

Any conventional carrier or excipient may be used in the pharmaceutical compositions of this invention. The choice of a particular carrier or excipient, or combinations of carriers or excipients, will depend on the mode of administration being used to treat a particular patient or type of bacterial infection. In this regard, the preparation of a suitable pharmaceutical composition for a particular mode of administration, such as oral, topical, inhaled or parenteral administration, is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington's Pharmaceutical Sciences*, Mace Publishing Co., Philadelphia, Pa. 17th Ed. (1985) and "*Modern Pharmaceutics*," Marcel Dekker, Inc. $3^{rd}$ Ed. (G. S. Banker & C. T. Rhodes, Eds.).

The pharmaceutical compositions of this invention will typically contain a therapeutically effective amount of a compound of formula I or II or a pharmaceutically acceptable salt thereof. Typically, such pharmaceutical compositions will contain from about 0.1 to about 90% by weight of the active agent, and more generally from about 10 to about 30% of the active agent.

Preferred pharmaceutical compositions of this invention are those suitable for parenteral administration, particularly intravenous administration. Such pharmaceutical compositions typically comprise a sterile, physiologically-acceptable aqueous solution containing a therapeutically effective amount of a compound of formula I or II or a pharmaceutically-acceptable salt thereof.

Physiologically acceptable aqueous carrier solutions suitable for intravenous administration of active agents are well known in the art. Such aqueous solutions include, by way of example, 5% dextrose, Ringer's solutions (lactated Ringer's injection, lactated Ringer's plus 5% dextrose injection, acylated Ringer's injection), Normosol-M, Isolyte E, and the like.

Optionally, such aqueous solutions may contain a co-solvent, for example, polyethylene glycol; a chelating agent, for example, ethylenediamine tetraacetic acid; a solubilizing agent, for example, a cyclodextrin; an anti-oxidant, for example, sodium metabisulphite; and the like.

If desired, the aqueous pharmaceutical compositions of this invention can be lyophilized and subsequently reconstituted with a suitable carrier prior to administration. In a preferred embodiment, the pharmaceutical composition is a lyophilized composition comprising a pharmaceutically-acceptable carrier and a therapeutically effective amount of a compound of formula I or II, or a pharmaceutically-acceptable salt thereof. Preferably, the carrier in this composition comprises sucrose, mannitol, dextrose, dextran, lactose or a combination thereof. More preferably, the carrier comprises sucrose, mannitol, or a combination thereof.

In one embodiment, the pharmaceutical compositions of this invention contain a cyclodextrin. When used in the pharmaceutical compositions of this invention, the cyclodextrin is preferably hydroxypropyl-β-cyclodextrin or sulfobutyl ether β-cyclodextrin. In such formulations, the cyclodextrin will comprise about 1 to 25 weight percent; preferably, about 2 to 10 weight percent of the formulation. Additionally, the weight ratio of cyclodextrin to active agent will typically range from about 1:1 to about 10:1.

The pharmaceutical compositions of this invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be packaged in sterile, hermetically-sealed ampoules and the like.

The following formulations illustrate representative pharmaceutical compositions of the present invention:

Formulation Example A

A frozen solution suitable for preparing an injectable solution is prepared as follows:

| Ingredients | Amount |
| --- | --- |
| Active Compound | 10 to 1000 mg |
| Excipients (e.g., dextrose) | 0 to 50 g |
| Water for Injection Solution | 10 to 100 mL |

Representative Procedure: The excipients, if any, are dissolved in about 80% of the water for injection and the active compound is added and dissolved. The pH is adjusted with 1 M sodium hydroxide to 3 to 4.5 and the volume is then adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The vial is capped, labeled and stored frozen.

Formulation Example B

A lyophilized powder suitable for preparing an injectable solution is prepared as follows:

| Ingredients | Amount |
| --- | --- |
| Active Compound | 10 to 1000 mg |
| Excipients (e.g., mannitol and/or sucrose) | 0 to 50 g |
| Buffer Agent (e.g., citrate) | 0 to 500 mg |
| Water for Injection | 10 to 100 mL |

Representative Procedure: The excipients and/or buffering agents, if any, are dissolved in about 60% of the water for injection. The active compound is added and dissolved and the pH is adjusted with 1 M sodium hydroxide to 3 to 4.5 and the volume is adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The formulation is then freeze-dried using an appropriate lyophilization cycle. The vial is capped (optionally under partial vacuum or dry nitrogen), labeled and stored under refrigeration.

Formulation Example C

An injectable solution for intravenous administration to a patient is prepared from Formulation Example B above as follows:

Representative Procedure: The lyophilized powder of Formulation Example B (e.g., containing 10 to 1000 mg of active compound) is reconstituted with 20 mL of sterile water and the resulting solution is further diluted with 80 mL of sterile saline in a 100 mL infusion bag. The diluted solution is then administered to the patient intravenously over 30 to 120 minutes.

Utility

The cross-linked glycopeptide—cephalosporin compounds of the invention are useful as antibiotics. For example, the compounds of this invention are useful for treating or preventing bacterial infections and other bacteria-related medical conditions in mammals, including humans and their companion animals (i.e., dogs, cats, etc.) that are caused by microorganisms susceptible to the compounds of this invention.

Accordingly, in one of its method aspects, the invention provides a method of treating a bacterial infection in a mammal, the method comprising administering to a mammal in need of such treatment, a pharmaceutical composition comprising a pharmaceutically-acceptable carrier and a therapeutically effective amount of a compound of formula I or II, or a pharmaceutically-acceptable salt thereof.

By way of illustration, the compounds of this invention are particularly useful for treating or preventing infections caused by Gram-positive bacteria and related microorganisms. For example, the compounds of this invention are effective for treating or preventing infections caused by certain *Enterococcus* spp.; *Staphylococcus* spp., including coagulase negative staphylococci (CNS); *Streptococcus* spp.; *Listeria* spp.; *Clostridium* ssp.; *Bacillus* spp.; and the like. Examples of bacterial species effectively treated with the compounds of this invention include, but are not limited to, methicillin-resistant *Staphylococcus aureus* (MRSA);

methicillin-susceptible *Staphylococcus aureus* (MSSA); glycopeptide intermediate-susceptible *Staphylococcus aureus* (GISA); methicillin-resistant *Staphylococcus epidermitis* (MRSE); methicillin-sensitive *Staphylococcus epidermitis* (MSSE); vancomycin-sensitive *Enterococcus faecalis* (EFSVS); vancomycin-sensitive *Enterococcus faecium* (EFMVS); penicillin-resistant *Streptococcus pneumoniae* (PRSP); *Streptococcus pyogenes*; and the like.

As shown in Table 2 of Example 16 below, several invention compounds, Ia–f, Im and In, were more effective than vancomycin against methicillin-sensitive *Staphylococcus aureus* and methicillin-resistant *Staphylococcus aureus*, by a factor of 10 or more. The compounds were also significantly more active than their des-chloro analogs Ig, Ij, and Ik, although these compounds were also more active than vancomycin. In a "time-kill" assay, as described in Example 17, a compound of formula I, i.e. compound Ib, was bactericidal against MRSA at a concentration of <1.0 µg/mL in 4 hours. By comparison, vancomycin was bactericidal against MRSA at a concentration of 4 µg/mL in 24 hours. In an in vivo assay in neutropenic mice, as described in Example 18, a compound of formula I, i.e. compound 1b, had an $ED_{50}$ of <0.1 mg/kg, iv, compared to an $ED_{50}$ of 9 mg/kg, iv, for vancomycin.

In general, the compounds of the invention are preferred for treating or preventing infections caused by strains of bacteria that are susceptible to either glycopeptides or cephalosporins.

Representative types of infections or bacteria-related medical conditions which can be treated or prevented with the compounds of this invention include, but are not limited to, skin and skin structure infections, urinary tract infections, pneumonia, endocarditis, catheter-related blood stream infections, osteomyelitis, and the like. In treating such conditions, the patient may already be infected with the microorganism to be treated or merely be susceptible to infection in which case the active agent is administered prophylactically.

The compounds of this invention are typically administered in a therapeutically effective amount by any acceptable route of administration. Preferably, the compounds are administered parenterally. The compounds may be administered in a single daily dose or in multiple doses per day. The treatment regimen may require administration over extended periods of time, for example, for several days or for one to six weeks or longer. The amount of active agent administered per dose or the total amount administered will typically be determined by the patient's physician and will depend on such factors as the nature and severity of the infection, the age and general health of the patient, the tolerance of the patient to the active agent, the microorganism(s) causing the infection, the route of administration and the like.

In general, suitable doses will range of from about 0.25 to about 10.0 mg/kg/day of active agent, preferably from about 0.5 to about 2 mg/kg/day. For an average 70 kg human, this would amount to about 15 to about 700 mg per day of active agent, or preferably about 35 to about 150 mg per day.

Additionally, the compounds of this invention are effective for inhibiting the growth of bacteria. In this embodiment, bacteria are contacted either in vitro or in vivo with a growth-inhibiting amount of a compound of formula I or II or pharmaceutically acceptable salt thereof. Typically, a growth-inhibiting amount will range from about 0.008 µg/mL to about 50 µg/mL; preferably from about 0.008 µg/mL to about 25 µg/mL; and more preferably, from about 0.008 µg/mL to about 10 µg/mL. Inhibition of bacterial growth is typically evidenced by a decrease or lack of reproduction by the bacteria and/or by lysis of the bacteria, i.e., by a decrease in colony-forming units in a given volume (i.e., per mL) over a given period of time (i.e., per hour) compared to untreated bacteria.

The compounds of this invention are also effective for inhibiting cell wall biosynthesis in bacteria. In this embodiment, bacterial are contacted either in vitro or in vivo with a cell wall biosynthesis-inhibiting amount of a compound of formula I or II or pharmaceutically acceptable salt thereof. Typically, a cell wall biosynthesis-inhibiting amount will range from about 0.04 µg/mL to about 50 µg/mL; preferably from about 0.04 µg/mL to about 25 µg/mL; and more preferably, from about 0.04 µg/mL to about 10 µg/mL. Inhibition of cell wall biosynthesis in bacteria is typically evidenced by inhibition or lack of growth of the bacteria including lysis of the bacteria.

Additionally, compounds of this invention have been found to have surprising and unexpectedly rapid cidality against certain bacteria, including methicillin-resistant *Staphylococci aureus* (MRSA) and methicillin-resistant *Staphylococci epidermitis* (MRSE). These properties, as well as the antibiotic utility of the compounds of this invention, can be demonstrated using various in vitro and in vivo assays well known to those skilled in the art. For example, representative assays are described in further detail in the following Examples.

EXAMPLES

The following synthetic and biological examples are offered to illustrate this invention and are not to be construed in any way as limiting the scope of this invention.

In the examples below, the following abbreviations have the following meanings unless otherwise indicated. Abbreviations not defined below have their generally accepted meaning.

BOC=tert-butoxycarbonyl
CFU=colony-forming units
DCM=dichloromethane
DIPEA=diisopropylethylamine
DMF=N,N-dimethylformamide
DMSO=dimethyl sulfoxide
EtOAc=ethyl acetate
HOBT=1-hydroxy benzotriazole
HOAT=1-hydroxy-7-azabenzotriazole
HPLC=high performance liquid chromatography
MIC=minimum inhibitory concentration
MS=mass spectrometry
PMB=p-methoxybenzyl
PyBOP=benzotriazol-1-yloxytripyrrolidinophosphonium hexafluorophosphate
THF=tetrahydrofuran
TLC=thin layer chromatography
TFA=trifluoroacetic acid All temperatures reported in the following examples are in degrees Celsius (° C.) unless otherwise indicated. Also, unless noted otherwise, reagents, starting materials and solvents were purchased from commercial suppliers (such as Aldrich, Fluka, Sigma and the like) and were used without further purification. Vancomycin hydrochloride semi-hydrate was purchased from Alpharma, Inc., Fort Lee, N.J. 07024 (Alpharma AS, Oslo, Norway).

Reverse-phase HPLC was typically conducted using a $C_{18}$ column and (A) 98% water, 2% acetonitrile, 0.1% TFA, with an increasing gradient (e.g., 0 to about 70%) of (B) 10% water, 90% acetonitrile, 0.1% TFA, unless otherwise stated.

In the syntheses described below, intermediates 4a–4g are defined as follows. In each of these compounds, n is 0 and $R^a$ is —$CH_2$—.

| Cmpd. | W | $R^9$ | $R^a$ subst. | $R^2$ |
|---|---|---|---|---|
| 4a | C–Cl | $CH_3$ | para | $CH_2CH_3$ |
| 4b | C–Cl | $CH_3$ | para | H |
| 4c | C–Cl | $CH_3$ | meta | H |
| 4d | C–H | $CH_3$ | para | H |
| 4e | C–H | $CH_3$ | meta | H |
| 4f | N | $CH_3$ | para | H |
| 4g | C–Cl | H | para | H |

Example 1

Preparation of 4a: (7R)-7-[(Z)-2-(2-Amino-5-chlorothiazol-4-yl)-2-(methoxyimino)acetamido]-3-[((4-(ethylamino)methyl)-1-pyridinio)methyl]-3-cephem-4-carboxylate Bis-trifluoroacetic Acid Salt (see FIGS. 2 and 3).

A. Preparation of 2-Amino-5-chloro-α-(methoxyimino)-4-thiazoleacetic Acid (6)

To 500 mL of acetic acid were added 40.0 g (0.20 mol) of 2-amino-α-(methoxyimino)-4-thiazoleacetic acid (Aldrich Chemical Company, Milwaukee, Wis.) and 27.9 g (0.21 mol) N-chlorosuccinimide. The mixture was heated in a 70° C. bath. The solids dissolved within 30 minutes, and after 45 minutes the reaction was complete by MS. The dark solution was allowed to cool to room temperature and concentrated under vacuum to give a dark solid, which was used without purification.

B. Preparation of Cephalosporin Derivative (8)

To 47.5 g (0.20 mol) of (6) in 700 mL of DMF was added 81.1 g (0.20 mol) of the aminocephalosporonic ester (7) (Otsuka, Osaka, JP) and 27.0 g (0.20 mol) of HOAt. The mixture was cooled to 0° C., and 26.7 g (0.22 mol) of 2,4,6-collidine was added. To this solution was added 42.2 g (0.22 mol) of 1-(3-dimethylaminopropyl)-3-ethylcarbodiimide hydrochloride (EDAC). After five hours, the solution was partitioned between 1:1 EtOAc/ether and water, and the phases were separated. The aqueous solution was back-extracted twice with EtOAc. The combined organic phases were washed once each with 0.5 M citric acid, water, 50% saturated $NaHCO_3$, water, and brine. The organic phase was dried over $MgSO_4$, filtered, and concentrated in vacuo. The residue was dissolved in a minimum volume of methylene chloride, and the product was precipitated by pouring the solution into ether. The solids were isolated by filtration to give 48 g of the compound (8).

Analytical Data: MS m/z calc. 586.04, obs. 586.2 (M+1); $^1$H NMR (DMSO-$d_6$): d 9.60 (d, 1H), 7.35 (m, 3H), 6.91 (d, 2H), 5.82 (m, 1H), 5.17 (m, 3H), 4.56 (m, 2H), 3.84 (s, 3H), 3.76 (s, 3H), 3.62 (m, 2H).

C. Coupling to Pyridinium Moiety

To 48.5 g (82.7 mmol) of the chloromethylcephalosporin ester 8 and 40 mL of anisole in 400 mL of 1,2-dichloroethane was added 300 mL of TFA. After 40 minutes, the solution was concentrated to ½ volume in vacuo, and the product was precipitated by pouring the concentrate into 1 L of ether. The solids were isolated by filtration, rinsed with ether, and dried to give 42.5 g of crude free acid. This material (25.0 g, 53.6 mmol) was dissolved in 200 mL of 1:1 acetonitrile/DMF. To this solution were added 10.1 g (83.3 mmol) of 2,4,6-collidine and 15.2 g (64.5 mmol) of 4-(N-t-butoxycarbonyl)-ethylaminomethylpyridine (9) (prepared by conventional procedures from 4-ethylaminomethylpyridine, which is commercially available from Aldrich Chemical Company, Milwaukee, Wis.). After 3.5 hours, the product was precipitated by pouring the solution into 1 L of ether. The solids were isolated by filtration, washed with ether, and dried under vacuum to give 26 g of crude material. The product was purified by preparative reversed-phase HPLC to give compound 10 as an off-white powder.

Analytical Data: MS m/z calc. 666.12, obs. 666.2 (M+1); $^1$H NMR (DMSO-$d_6$): d 9.36 (d, 1H), 8.91 (d, 2H), 7.95 (d, 2H), 7.24 (b, 1H), 5.83 (m, 1H), 5.50 (m, 2H), 5.17 (d, 1H), 4.66 (s, 2H), 3.83 (s, 3H), 3.52 (d, 1H), 3.30 (m, 3H), 1.37 (s, 9H), 1.08 (t, 3H).

D. Deprotection of 10

To 610 mg (0.78 mmol) of compound 10 and 1 mL of anisole was added 8 mL of trifluoroacetic acid. After 20 minutes, the product was precipitated by pouring the reaction into 100 mL of ether. The solids were isolated by filtration, washed with ether, and dried under vacuum to give 4a as a light yellow solid.

Analytical Data: $^1$H NMR (DMSO-$d_6$): d 9.56 (d, 1H), 9.44 (br, 1H), 9.10 (d, 2H), 8.21 (d, 2H), 7.38 (b, 1H), 5.86 (m, 1H), 5.54 (m, 2H), 5.15 (d, 1H), 4.51 (s, 2H), 3.80 (s, 3H), 3.40 (m, 2H), 3.30 (m, 2H), 1.22 (t, 3H).

Example 2

Preparation of 4b: (7R)-7-[(Z)-2-(2-Amino-5-chlorothiazol-4-yl)-2-(methoxyimino)acetamido]-3-[(4-(aminomethyl)-1-pyridinio)methyl]-3-cephem-4-carboxylate Bis-trifluoroacetic Acid Salt A. Preparation of 2-Amino-5-chloro-α-(methoxyimino)-4-thiazoleacetic acid (6)

To 500 mL of DMF were added 50.0 g (250 mmol) of 2-amino-α-(methoxyimino)-4-thiazoleacetic acid and 35 g (260 mmol) of N-chlorosuccinimide. The mixture was stirred at room temperature overnight, after which time mass spectral analysis showed no more starting material to be present. The light brown solution was used without further manipulation.

B. Preparation of Cephalosporin Derivative (8)

To the solution of the acid 6 in DMF (101.5 g, 250 mmol) from step (a) was added the aminocephalosporonic ester 7 (34 g, 250 mmol). The mixture was cooled to 0° C., and 33.5 mL (250 mmol) of 2,4,6-collidine was added. To this solution was added 53 g (275 mmol) of 1-(3-dimethylaminopropyl)-3-ethylcarbodiimide hydrochloride. After 2 hours, the solution was precipitated into 3 L water and filtered. The solids were washed with water (2×1 L), saturated sodium bicarbonate (500 mL) and water (4×500 mL) and dried under vacuum. The dried solids were taken up in 500 mL methylene chloride at room temperature, and the solution was slowly stirred, forming a precipitate. The crystals were collected by filtration, washed with methylene chloride until the washings were no longer brown, and dried under vacuum to give the amide 8 (74 g).

C. Coupling to Pyridinium Moiety

Acetone (250 mL) was added to a mixture of 50 g (85 mmol) chloromethylcephalosporin ester 8 and 13 g (85 mmol) sodium iodide, under nitrogen in the dark. After stirring for 30 minutes, 27 g (130 mmol) of 4-(N-tert-butoxycarbonyl)aminomethyl pyridine and 30 mL acetone were added. After stirring an additional 2 hours, 1.4 L of 0.1 N HCl was added, producing a gummy precipitate. The solvent portion was decanted, and the gummy residue was treated with 800 mL water to give a solid. The water was decanted, and the solid was dissolved in 1 L of 4:1 ethyl acetate/ethanol. The solution was washed with 500 mL saturated brine, dried over magnesium sulfate, and evaporated to dryness to give 70 g (79 mmol, 93%) of the product (analogous to 10, with -NHBOC substituted for -NEtBOC) was obtained, having a purity of 78% as determined by HPLC (254 nm).

This material was deprotected, without further purification, as follows. The crude product (70 g, 79 mmol) was dissolved in 550 mL methylene chloride under nitrogen, and 35 mL (320 mmol) anisole was added, followed by 150 mL trifluoroacetic acid. After 2 hours, the mixture was concentrated under vacuum. The product precipitated on addition of 1 L diethyl ether. The solids were isolated by filtration, washed with ether, stirred in 200 mL water, and filtered. The filtrate was lyophilized to dryness and purified by reverse-phase HPLC, yielding 30 g (approx. 50%) 4b.

Example 3

Preparation of 2a: C-Aminoethylamide Vancomycin (Structure 2 where $R^2$, $R^5$, $R^6$, $R^8$ are H; $R^4$ is OH; $R^7$ is Me $X^1$, $X^2$ are Cl; $R^d$ is H; $R^e$ is —CH$_2$CH$_2$—)

Figure 3:
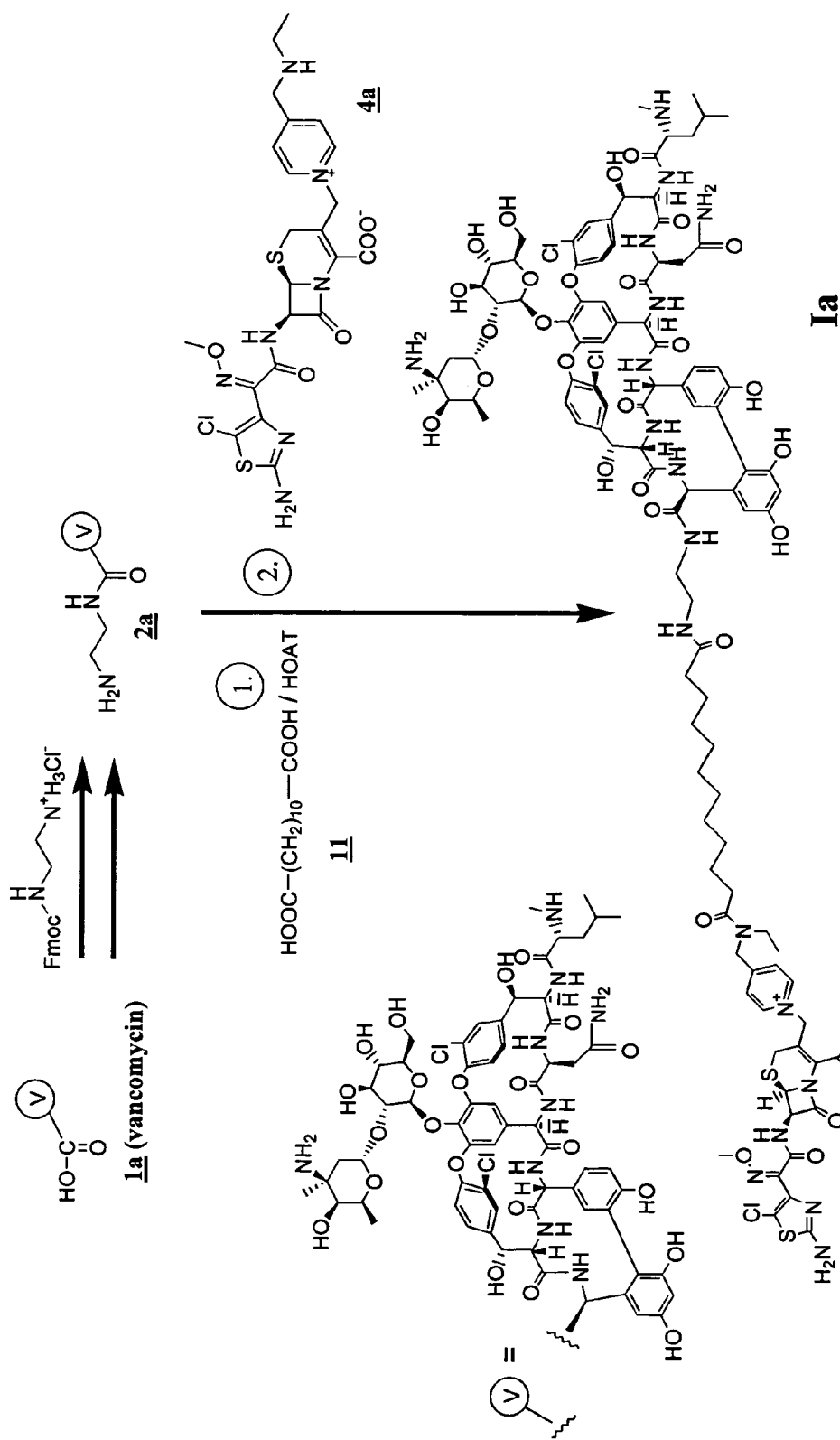
FIGS. 3 to 6 show synthetic schemes for preparing representative cross-linked glycopeptide-cephalosporin antibiotics, designated herein as Ia, Ib, Id, and Ie, respectively.
Figure 4:
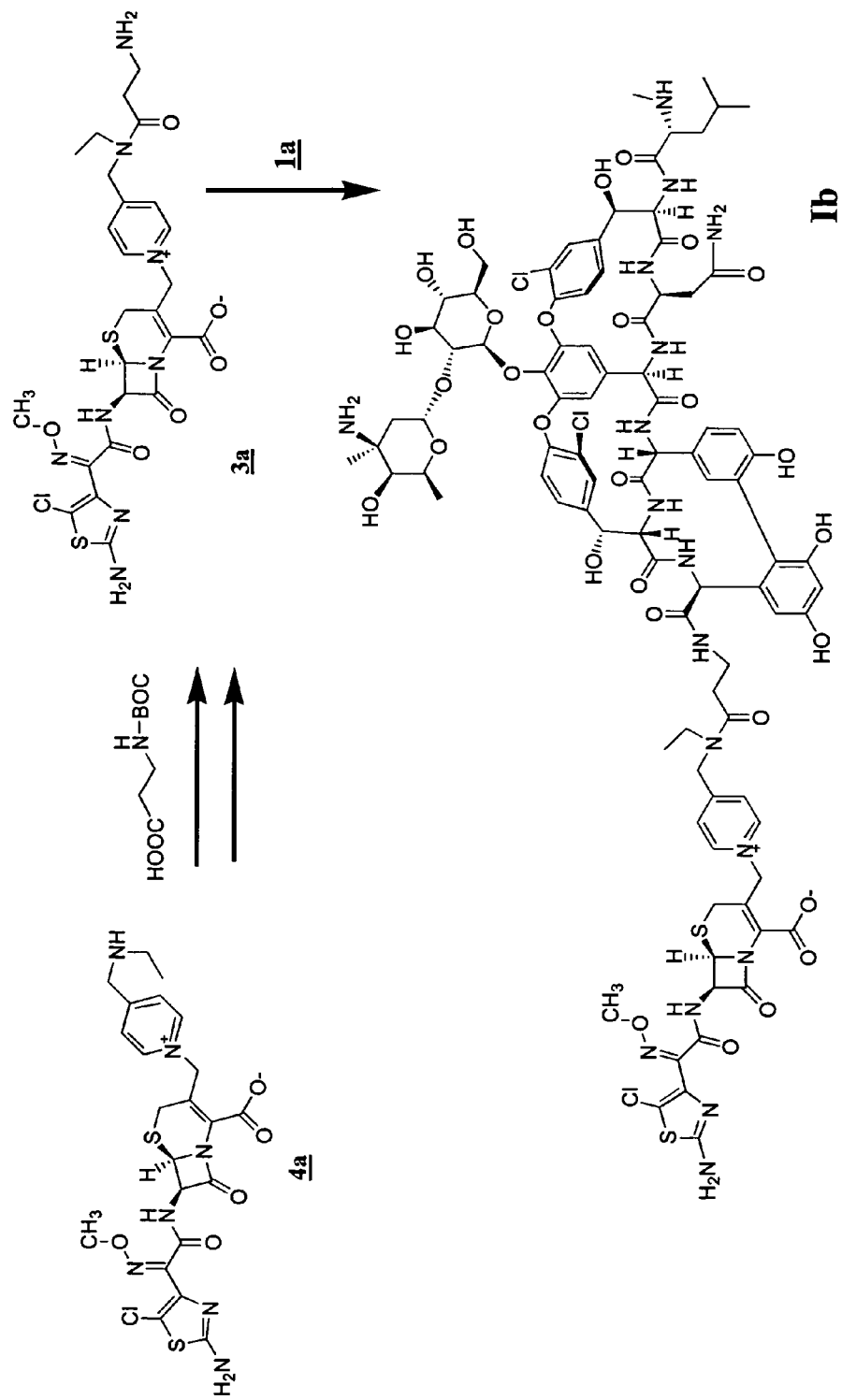

To a solution of vancomycin hydrochloride monohydrate (7.3 g, 4.7 mmol) in 75 mL of DMSO was added, at room temperature, 4.1 mL (23.5 mmol) DIPEA, followed by 1.8 g (5.6 mmol) 9-fluorenylmethyl N-(2-aminoethyl)carbamate hydrochloride (Fmoc-NH—CH$_2$—CH$_2$—NH$_3$Cl) (see FIG. 3). A solution of PyBOP (2.7 g, 5.2 mmol) and HOBT (0.63 g, 4.7 mmol) in 75 mL of N,N'-dimethylpropyleneurea (DMPU) was then added dropwise rapidly. The resulting solution was stirred at room temperature for 2 hrs, then poured into 800 mL of diethyl ether to give a gum. The ether was decanted and the gum washed with additional ether to give crude [C]-(2-Fmoc-aminoethyl) vancomycin.

This product (Fmoc-2a) was taken up in 40 mL of DMF and 10 mL of piperidine was added, and the solution was left to stand at room temperature for 20 minutes, then added dropwise to 450 mL acetonitrile, forming a precipitate. The mixture was centrifuged, the acetonitrile decanted, and the residue washed twice with 450 mL of acetonitrile and once with 450 mL of diethyl ether and then air dried. The residue was then taken up in water, acidified to pH <5 with 3N HCl, and purified by reverse-phase HPLC, using a gradient of 2 to 30% acetonitrile in water containing 0.1% trifluoroacetic acid. This gave the product 2a as the tri(TFA) salt.

Example 4

Preparation of Compound Ia

Pyridinium lactam bis-trifluoroacetate 4a (2.4 g), prepared as described in Example 1 above, was dissolved in N,N-dimethylformamide (DMF, 40 mL) under nitrogen and cooled to 0° C. Dodecanedioic acid bis-1-hydroxy-7-azatriazole ester (7.0 g) was added (1), followed by 2,4,6-collidine (1.2 mL), and the mixture was stirred for 65 minutes, then added to ethyl acetate (50 mL), and this mixture precipitated into diethyl ether (400 mL). The activated ester lactam 5a was collected by filtration and dried under vacuum, and a portion (14 mg) was dissolved in DMF (122 µL) and added at 0° C. to a mixture of C-aminoethylamide vancomycin tritrifluoroacetate, 2a (50 mg), prepared as described in Example 3, and 2,4,6-collidine (5.4 µL) in DMF (500 µL). The mixture was kept at 0° C. for 20 minutes, then trifluoroacetic acid was added (7.3 µL). The mixture was kept at -20° C. overnight, then purified by reverse-phase HPLC to give the product Ia.

Analytical Data: MS m/z obs. 2252.8, calc. 2252.7.

Example 5

Preparation of Compound Ib

At room temperature under nitrogen, 1-(3-dimethylaminopropyl)-3-ethyl carbodiimide hydrochloride (740 mg), 1-hydroxy-7-azatriazole (520 mg) and N-(tert-butoxycarbonyl)-β-alanine (660 mg) were stirred in DMF (10 mL) for 7 hours, then cooled to 0° C. Pyridinium lactam bis-trifluoroacetate 4a (2 g) (see Example 1) was added and stirred until it had fully dissolved, then 2,4,6-collidine (700 µL) was added, and the mixture was stirred at 0° C. for 100 minutes. Trifluoroacetic acid (700 µL) and water (30 mL) were added, and the product was purified by reverse-phase HPLC. After lyophilization, the product was treated with 20 mL of 50% trifluoroacetic acid/dichloromethane for 40 minutes. The lactam amine 3a (see FIG. 4) was recovered as its bis-trifluoroacetate salt on precipitation into diethyl ether, and dried under vacuum.

Vancomycin hydrochloride monohydrate, 1a (900 mg) (Structure 1 where $R^5$, $R^6$, $R^8$ are H; $R^4$ is OH; $R^7$ is Me; $X^1$, $X^2$ are Cl; also referred to in Figures as "vancomycin") was dissolved in dimethyl sulfoxide (5 mL) under nitrogen at room temperature, and 1-hydroxy-7-azatriazole was added (80 mg), followed by PyBOP (300 mg) in DMF (5 mL) and N,N-diisopropylethylamine (100 µL). The mixture was stirred for 20 minutes, trifluoroacetic acid (45 µL) was added, and the mixture was cooled to 0° C. Pyridinium lactam amine 3a (250 mg) was added, followed by 2,4,6-collidine (270 µL), and the mixture was stirred at 0° C. for 30 minutes, then precipitated into acetonitrile. The crude product was collected by centrifugation and purified by reverse-phase HPLC to give Ib.

Analytical Data: MS m/z obs. 2069.7, calc. 2069.4.

Example 6

Preparation of Compound Ic

This compound was prepared according to the procedure described in Example 5, substituting 6-(N-BOC)amino hexanoic acid for N-BOC-β-alanine.

Analytical Data: MS m/z obs. 2110.5, calc. 2111.5

Example 7

Preparation of Compound Id

Figure 5:
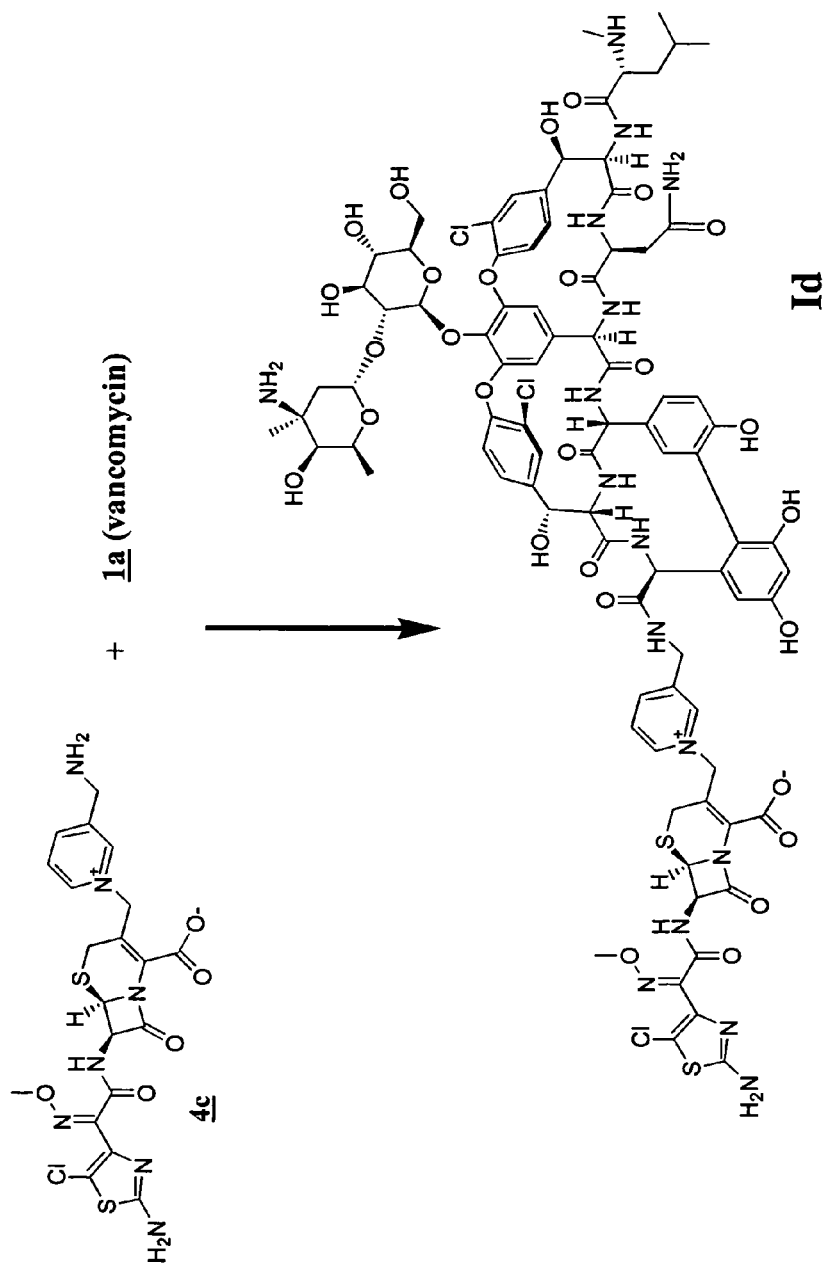

Vancomycin hydrochloride monohydrate, 1a (900 mg), was dissolved in dimethyl sulfoxide (5 mL) under nitrogen at room temperature, and 1-hydroxy-7-azatriazole was added (80 mg), followed by PyBOP (300 mg) in DMF (5 mL) and N,N-diisopropylethylamine (100 µL). The mixture was stirred for 20 minutes, trifluoroacetic acid (45 µL) was added, and the mixture was cooled to 0° C. Pyridinium lactam bis-trifluoroacetate 4c (250 mg) (identical to 4b with the exception of meta substitution on pyridine; see FIG. 5) was added, followed by 2,4,6-collidine (270 µL), and the mixture was stirred at 0° C. for 30 minutes, then precipitated into acetonitrile. The crude product was collected by centrifugation and purified by reverse-phase HPLC to give the product Id.

Analytical Data: MS m/z obs.1970.9, calc.1970.3.

Example 8

Preparation of Compound Ie

A. Preparation of 3b (structure 3 where W is Cl, $R^9$ is Me, n is 0, $R^a$ is $CH_2$, $R^b$ is hydrogen, $R^c$ is —$CH_2CH(COOH)$—, $R^2$ is hydrogen, and x is 1)

HOAT (56 mg, 0.2 mmol), PyBOP (208 mg, 0.2 mmol) and N-BOC aspartic acid α-tert-butyl ester was dissolved in DMF (500 µL). DIPEA (70 µL, 0.2 mmol) was then added, and the reaction was stirred at room temperature for 20 minutes. The reaction was then cooled to –10° C., and TFA (32 µL, 0.2 mmol) was added. The C3-pyridinium cephalosporin 4b (306 mg, 0.2 mmol) was added to the reaction as a solution in DMF (500 µL). Collidine (160 µL, 0.6 mmol) was added and the reaction was stirred for 1 hr at –10° C. The reaction mixture was concentrated in vacuo, then purified using reverse phase HPLC (10–90% gradient over 60 minutes) to provide, on lyophilization, the protected cephalosporin aspartic acid derivative TFA salt as a white amorphous powder (193 mg). This product (162 mg) was dissolved in TFA (10 mL) and stirred at room temperature for 60 minutes. The reaction was concentrated in vacuo, and the residue was dissolved in $CH_3CN/H_2O$ (1:1;0.1% TFA) and lyophilized to provide the desired deprotected cephalosporin aspartic acid derivative (3b) TFA salt as a white solid (92 mg).

Analytical Data: MS m/z 652.9 ($MH^+$).

B. Reaction of 3b with Vancomycin

Figure 6:
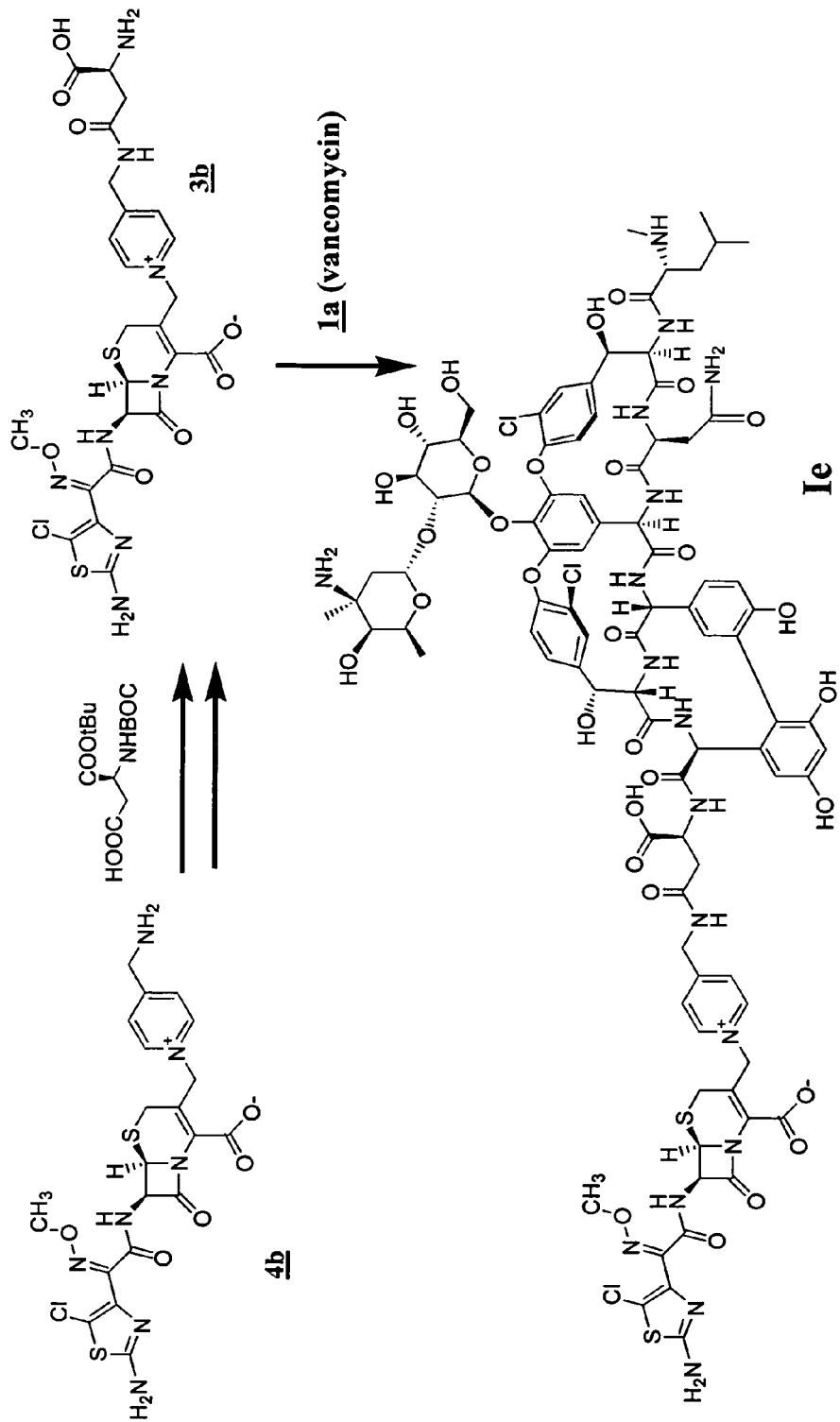

Vancomycin hydrochloride, 1a (0.32 g, 0.21 mmol), was dissolved in 3 mL of DMSO. A 0.5 mL solution of PyBOP (0.11 g, 0.21 mmol) and HOAT (0.03 g, 0.21 mmol) in DMF was added, followed by DIPEA (0.04 mL, 0.21 mmol). The reaction was stirred 30 minutes, then TFA (0.02 mL, 0.21 mmol) was added, and the mixture was cooled to 0° C. A solution of 3b (0.15 g, 0.17 mmol) (see FIG. 6) in DMF (1 mL) was then added, followed by collidine (0.08 mL, 0.63 mmol). The reaction was stirred at 4° C. overnight and then precipitated from EtOAc, centrifuged and the resulting solid washed with MeCN. The desired compound was purified by HPLC (2–30% MeCN) to give 0.3 g of Ie as a white solid.

Analytical Data: MS m/z 1042.6 $[(M+2H)/2)]^{2+}$.

Example 9

Preparation of Compound If

To a solution of 0.6 mL of DMSO containing vancomycin hydrochloride, 1a (134.0 mg, 0.09 mmol), and HOAT (12.3 mg, 0.09 mmol) was added a solution of PyBOP (46.9 mg, 0.09 mmol) in 0.6 mL of DMF, followed by addition of diisopropylethylamine (31.4 µL, 0.2 mmol). After stirring at ambient temperature for 20 min, the reaction mixture was treated with TFA (13.9 µL, 0.2 mmol) while cooling at 0° C. To this activated ester of vancomycin was added 69 mg (0.09 mmol) of pyridinium lactam 4a and collidine (51.3 µL, 0.4 mmol). The final mixture was allowed to stir at room temperature for 3 h, prior to quenching with TFA (33.4 µL, 0.40 mmol). The crude product was precipitated from the reaction mixture by adding ethyl acetate. The solid was collected by spinning down, dried, and purified by preparative HPLC. The desired product If was obtained as a white fluffy solid (89 mg).

Analytical Data: Retention time (anal. HPLC: 10 to 70% $MeCN/H_2O$ over 6 min)=2.00 min. MS m/z calcd. 1970.27 ($C_{86}H_{94}Cl_3N_{16}O_{28}S_2$); obsd. 985.7 $[(M+2H)/2]^{2+}$.

Example 10

Preparation of Compound Ik (a des-chloro analog of Compound If)

Figure 7:
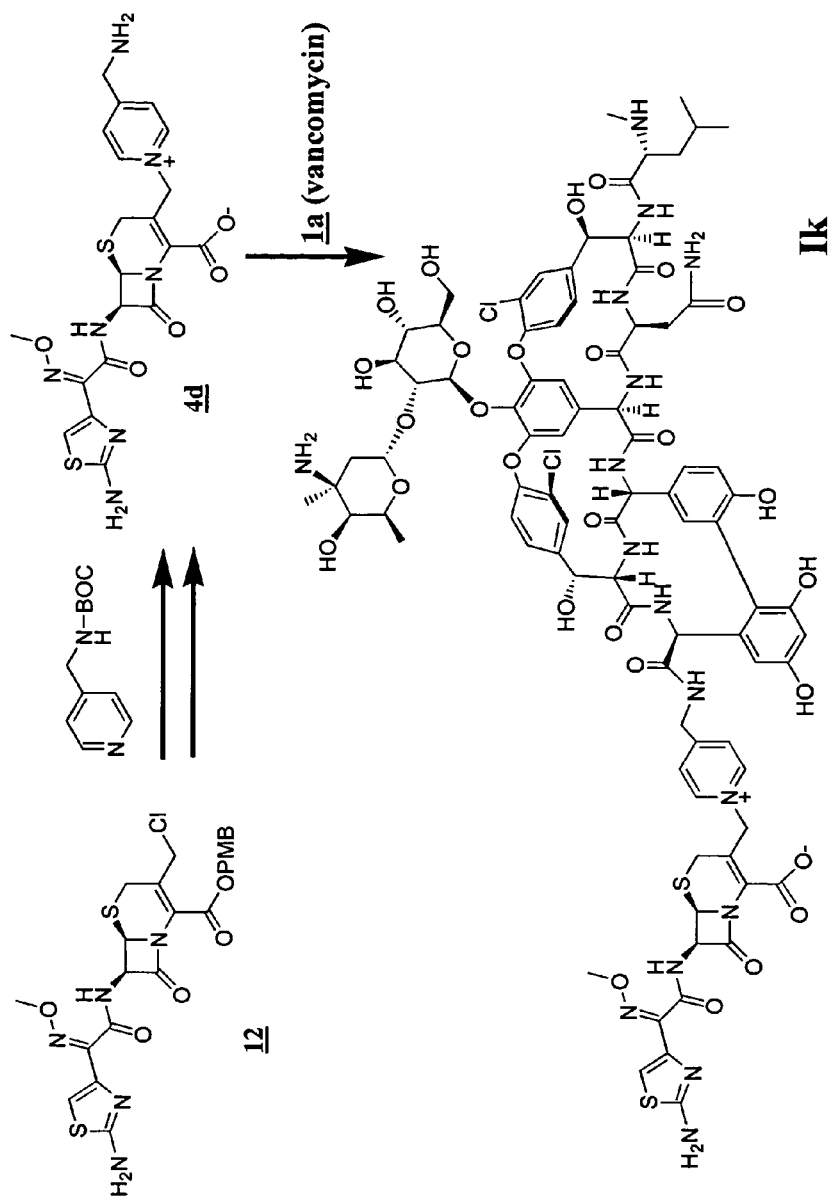
FIGS. 7 and 8 show synthetic schemes for preparing comparative des-chloro analogs of cross-linked glycopeptide-cephalosporin antibiotics.

Sodium iodide (0.271 g, 1.81 mmol) was added to a solution of cephalosporin-β-lactam 12 (0.999 g, 1.81 mmol) (see FIG. 7) dissolved in acetone (25 mL), protected from light and stirred under nitrogen. After 25 minutes, 4-(N-BOC-aminomethyl)pyridine (0.390 g, 1.87 mmol) was added, and the reaction was stirred for 2 hours. The product was precipitated with a large excess of ethyl acetate and recovered by filtration.

The product (0.353 g, 0.488 mmol) was dissolved in DCM (2.5 mL) and anisole (0.21 mL, 1.93 mmol) and TFA (1.5 mL, 19.47 mmol) were added. The reaction mixture was then stirred for 45 minutes at room temperature under nitrogen. The product was precipitated using diethyl ether, centrifuged, and the pellet washed twice with diethyl ether and dried. The product was dissolved in water and insolubles were filtered off. The aqueous material was lyophilized to afford 0.166 g of the TFA salt of 4d as an orange solid (identical to 4b with the exception that W=CH).

Analytical Data: MS m/z 504.1 (M+1); HPLC (2–30 acetonitrile/water, 254 nm) retention time=0.270 min.

HOAt (0.0626 g, 0.460 mmol) was added to a solution of vancomycin hydrochloride (0.7078 g, 0.455 mmol) in DMSO (3.5 mL). PyBOP (0.2338 g, 0.449 mmol) dissolved in DMF (3.5 mL) and DIPEA (79.0 µL, 0.453 mmol) were added, and the reaction was stirred at room temperature under nitrogen for 20 minutes, followed by addition of TFA (35.0 µL, 0.454 mmol). The reaction was then cooled in an ice bath. Lactam amine 4d (0.166 g, 0.227 mmol) was added, and upon dissolution collidine (180.0 µL, 1.365 mmol) was added. After 50 minutes of stirring, TFA (125.0 µL, 1.62 mmol) was added, and the product was precipitated with acetonitrile and centrifuged. The pellet was redissolved in a minimal amount of DMF and reprecipitated with acetonitrile three times, then dried under vacuum to give 0.8 g crude product. The crude product was purified by prep HPLC (2–35 acetonitrile/water), and fractions containing compound Ik were collected and lyophilized. Analytical Data: MS m/z 1539.6 (fragment), HPLC: (2–30 acetonitrile/water, 254 nm) retention time=2.92 min.

Example 11

Preparation of Compound Ig (a des-chloro analog of Compound Ib)

A. Preparation of N-Ethyl-N-(4-pyridylmethyl)-3-(N-BOC)-amino Propanamide (13)

To a solution of N-t-BOC-β-alanine (4.678 g, 24.7 mmol) in DCM (50 mL) was added diisopropylcarbodiimide (3.87 g, 24.7 mmol). The mixture was cooled in an ice bath and 4-(ethylaminomethyl)pyridine (3.37 g) was added. The reaction mixture was then stirred for 3.5 hours. The solid was removed by filtration, and the filtrate was washed with water and dried under vacuum to give 5.34 g of the title intermediate.

Analytical Data: MS m/z 308.1 (M+1).

B. Preparation of Compound Ig

Figure 8:
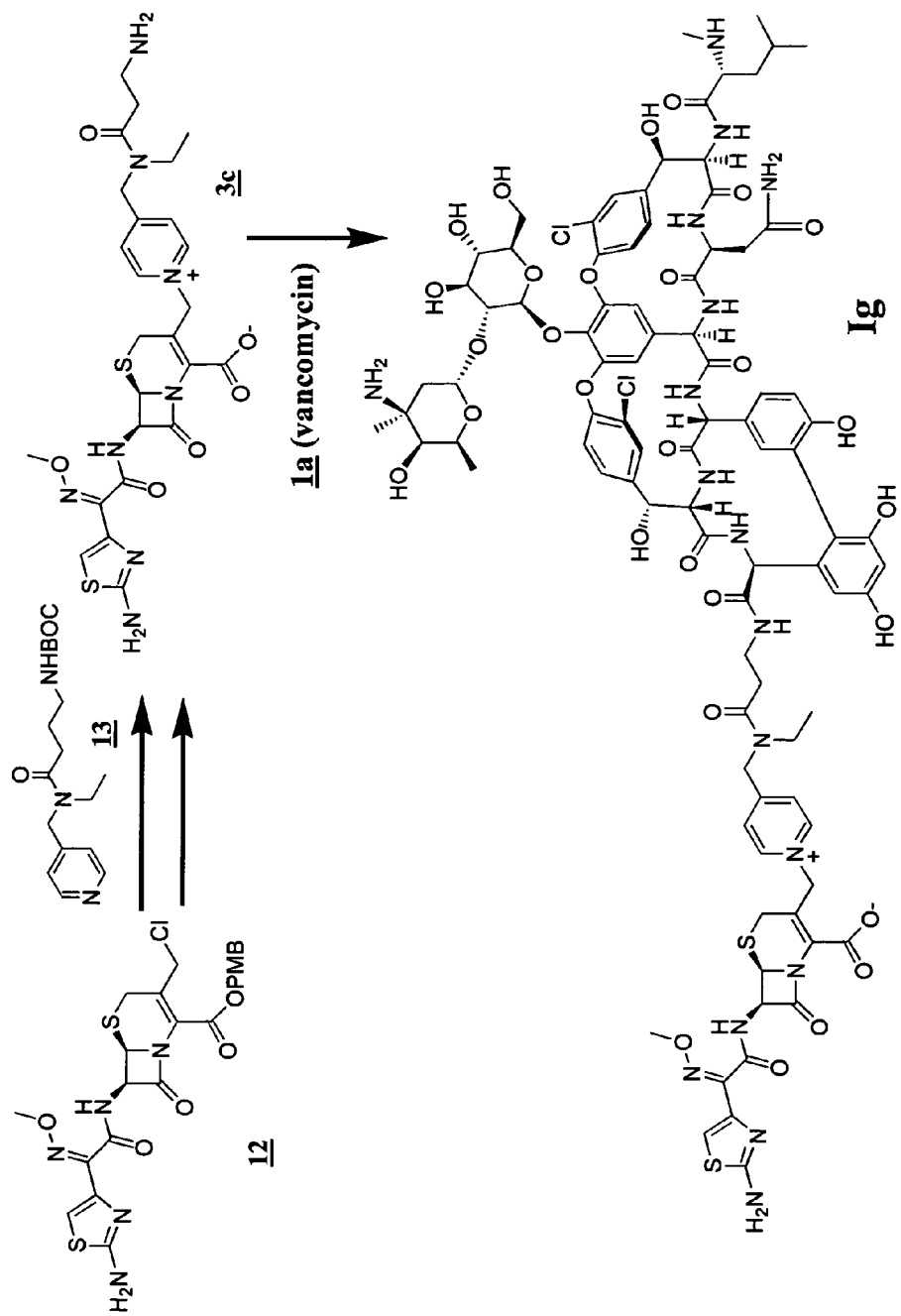

Sodium iodide (0.485 g, 3.22 mmol) was added to a solution of cephalosporin-β-lactam 12 (2.031 g, 3.22 mmol) (see FIG. 8) dissolved in acetone (50 mL) protected from light and under nitrogen. After 20 minutes, 13, prepared as described above, (1.29 g, 3.40 mmol) in acetone (10 mL) was added, and the reaction was stirred for 6 hours. The product was precipitated with a large excess of ethyl acetate and recovered by filtration. This product (1.70 g, 1.90 mmol) was dissolved in DCM (5 mL) and anisole (0.825 mL, 7.6 mmol) and TFA (5 mL, 64.9 mmol) were added. The reaction mixture was then stirred for 1 hour at room temperature under nitrogen. The product was precipitated using diethyl ether, centrifuged and the pellet washed twice with diethyl ether and dried, to give 1.7 g of the TFA salt of 3c (identical to 3a with the exception that W is CH).

Analytical Data: MS m/z 603.3 (M+1); HPLC (2–90 acetonitrile/water, 254 nm) retention time=3.42 min.

HOAt (0.560 g, 4.11 mmol) was added to a solution of vancomycin hydrochloride (6.350 g, 4.08 mmol) in DMSO (30 mL). PyBOP (2.127 g, 4.09 mmol) dissolved in DMF (30 mL) and DIPEA (0.711 mL, 4.08 mmol) were added, and the reaction was stirred at room temperature under nitrogen for 20 minutes, followed by addition of TFA (0.314 mL, 4.08 mmol). The reaction was then cooled in an ice bath. Lactam amine 3c (1.7 g, 2.04 mmol) dissolved in DMSO (25 mL) and DMF (10 mL) was added, and upon dissolution collidine (1.89 mL, 14.3 mmol) was added. The reaction was stirred for 50 minutes, TFA (1.26 mL, 16.3 mmol) was added, and the product was precipitated with acetonitrile and centrifuged down. The pellet was redissolved in a minimal amount of DMF and reprecipitated with acetonitrile three times, then dried under vacuum to give 7.4 g crude product. This crude product was purified by preparative HPLC (2–35 acetonitrile/water), and fractions containing the product, Ig, were collected and lyophilized.

Analytical Data: MS m/z 1639.5 (fragment), HPLC: (2–30 acetonitrile/water, 254 nm) retention time=3.76 min.

Example 12

Preparation of Compound Ij (a des-chloro analog of Compound Id)

Sodium iodide (1.4 g, 9.1 mmol) was added to (7R)-7-[(Z)-2-(2-amino-thiazol-4-yl)-2-(methoxyimino)acetamido]-3-(chloromethyl)-3-cephem-4-carboxylate (5 g, 9.1 mmol) in 35 mL of acetone. The reaction vessel was wrapped in foil and the mixture stirred for 1 hour. A solution of 3-aminomethylpyridine (2.8 g, 13.8 mmol) in 5 mL of acetone was added, and the reaction was stirred for 70 minutes and then precipitated into ether to give 5.4 g crude yield of 4e (identical to 4c with the exception that W is CH). This solid (4.4 g) was suspended in 20 mL of DCM, and 20 mL of TFA was added. The reaction mixture was stirred at room temperature for 90 minutes and then concentrated. The resulting oil was precipitated from ether and purified by preparative HPLC (2–10% MeCN) to give 0.6 g of the TFA salt of 4e, as a white fluffy solid.

Analytical Data: $R_t$=0.8 min (10–70% MeCN). $^1$H NMR (DMSO-$d_6$): δ 3.25 (dd, 2H), 3.8 (s, 3H), 4.2 (bs, 2H), 5.05 (d, 1H), 5.45 (dd, 2H), 5.8 (dd, 1H), 7.05 (s, 1H), 8.2 (m, 1H), 8.45 (bs, 2H), 8.6 (d, 1H), 9.0 (d, 1H), 9.05 (s, 1H), 9.4 (dd, 1H).

Vancomycin hydrochloride (0.73 g, 0.49 mmol) was dissolved in 2.5 mL of DMSO. A solution of PyBOP (0.23 g, 0.45 mmol) and HOAT (0.06 g, 0.45 mmol) was added in 2 mL of DMF, followed by DIPEA (0.16 mL, 0.82 mmol). The reaction was stirred for 25 minutes, then TFA (0.07 mL, 8.2 mmol) was added, and the reaction was cooled to 0° C. Collidine was added (0.22 mL, 1.6 mmol), followed by a solution of the above lactam 4e in 2 mL of DMF. The reaction was stirred for 2 h, then precipitated from ether and centrifuged. The product was purified by HPLC and then lyophilized to yield 0.23 g of the product, Ij.

Example 13

Preparation of Compound Im

2-Amino-α-(methoxyimino)-4-thiadiazoleacetic acid (15) (4.0 g, 19.8 mmol), prepared according to *J. Antibiotics* 53(10): 1061 (2000), was combined with cephalosporin derivative 14, prepared according to *Bull. Chem. Soc. Jpn.* 43:2925–33 (1970) (8.42 g, 20.79 mmol) (see FIG. 9) and HOAT (3.33 g, 21.78 mmol) in 50 mL DMF. The solution was purged with nitrogen and cooled to 0° C., and 1-(3-dimethylaminopropyl)-3-ethylcarbodiimide (3.99 g, 20.79 mmol) was added, followed by 1,3,5-collidine (2.75 mL, 20.79 mmol). The solution was stirred at 0° C. for 2 hours, then the reaction mixture was poured into 300 mL of water. The resulting solid was filtered, triturated with saturated aqueous NaHCO₃, refiltered, washed twice with water, and air-dried overnight to yield the cephalosporin intermediate 16 as an off-white powder. This compound was used without further purification.

Analytical Data: MS m/z calc. 553.01; obsd. 553.0 (M⁺, $^{35}$Cl), 555.0 (M⁺, $^{37}$Cl).

The chloro compound 16 (4.0 g, 7.23 mmol) was placed in a flask with 4-t-BOC-aminomethylpyridine (2.26 g, 10.85 mmol) and sodium iodide (1.08 g, 7.23 mmol) and purged with N₂. Acetone (60 mL) was added, and the reaction mixture was stirred at room temperature for 2 hours, then poured into 300 mL of 0.2 M HCl, resulting in the formation of a red gum on the sides of the flask. The acetone was decanted and the gum was dried under vacuum. Once dry, the residue was dissolved in 20 mL of DCM, and TFA (20 mL) was added. The reaction was stirred for one hour after which LC/MS analysis indicated the deprotection was complete. This solution was then poured into 200 mL of Et₂O, and the resulting precipitate was filtered, washed with Et₂O and dried under vacuum. Once dry, the crude solid was triturated in 100 mL of water for 3 hours. This solution was filtered, and the product was lyophilized to yield the crude compound 4f (identical to 4b with the exception that W is N) as a bis-TFA salt. The compound was used without further purification.

Analytical Data: MS m/z calc. 491.0; obsd. 491.5

Vancomycin hydrochloride (0.2 g, 0.135 mmol) and HOAt (20.6 mg, 0.135 mmol) were dissolved in 2 mL of DMSO. To this solution was added a solution of PyBOP (70.2 mg, 0.0135 mmol) in 2 mL of DMF. DIPEA (23.5 µL, 0.135 mmol) was added, and the solution was stirred at room temperature for 20 min. After this time, a solution of 4f (49 mg, 0.0675 mmol) in 1 mL of DMF was added, and the solution was cooled to 0° C. 1,3,5-Collidine (62.5 µL, 0.473 mmol) was then added, and the solution was stirred at 0° C. for 45 min. TFA (150 µL) was then added, and the solution was poured into 70 mL of $Et_2O$. The resulting precipitate was filtered, washed with $Et_2O$ and dried under vacuum. The product was purified by reverse-phase HPLC and isolated by lyophilization to afford Im as the tri-TFA salt.

Analytical Data: MS m/z calc.1937.8; obsd. 1937.6.

Example 14

Preparation of Compound In

Figure 10:
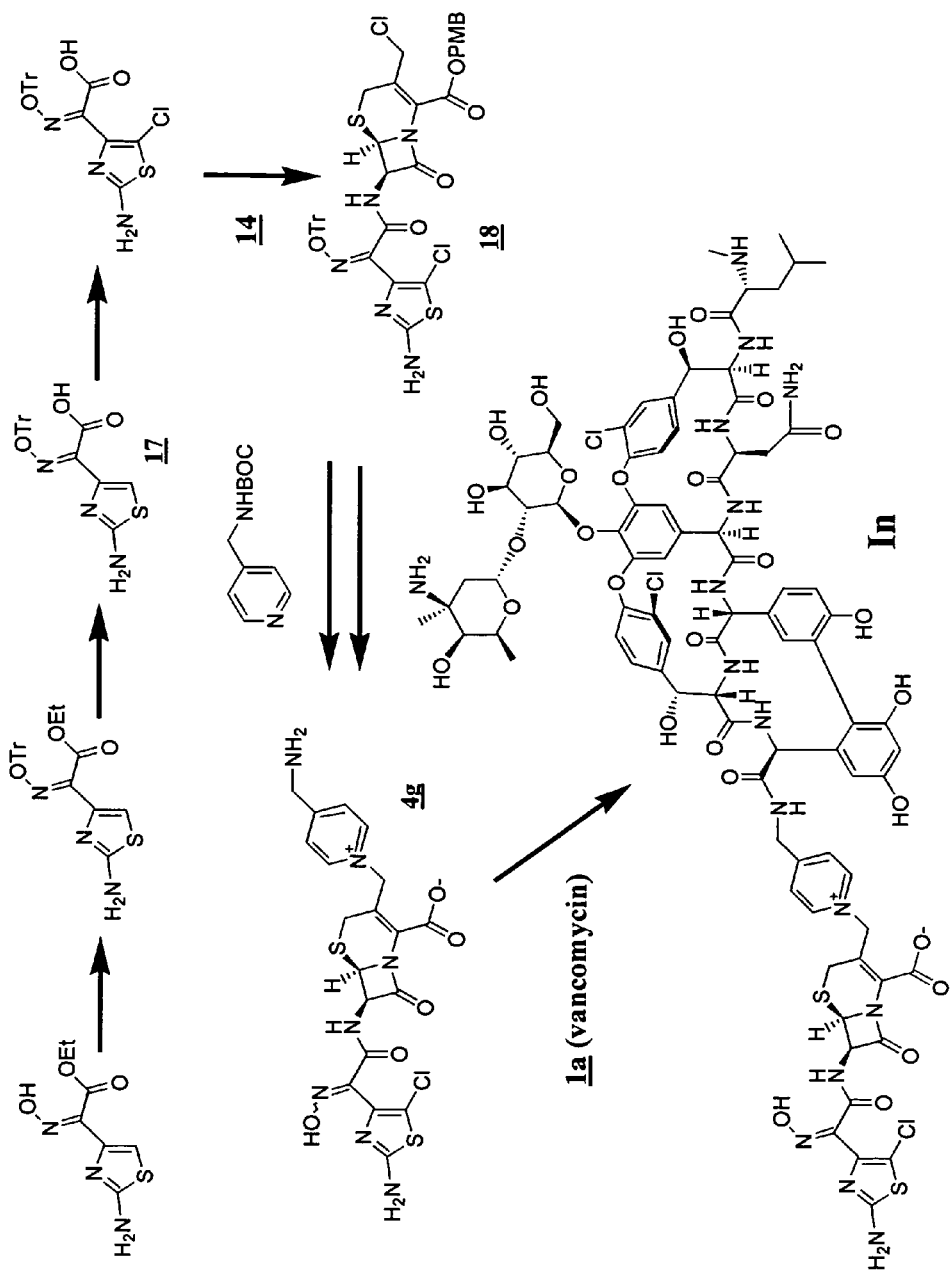

To a stirred solution of 2-amino-α-(trityloxyimino)-4-thiazole acetic acid (7) (15.60 g, 36.3 mmol) (prepared by tritylation of ethyl-2-amino-α-(hydroxyimino)-4-thiazoleacetate, followed by hydrolysis) in DMF (100 mL) was added 4.85 g (36.3 mmol) N-chlorosuccinimide (see FIG. 10). The reaction mixture was stirred at room temperature for 15 h, then poured into water (500 mL), and the precipitated solid was filtered and dried to yield the 5-chloro compound (15.11 g, 90%) as an off-white solid.

Analytical Data: $^1$H NMR (DMSO-d, 300 MHz): δ 7.18–7.33 (m, 15H); MS m/z obsd. 486.4 [M+Na]$^+$.

Figure 9:
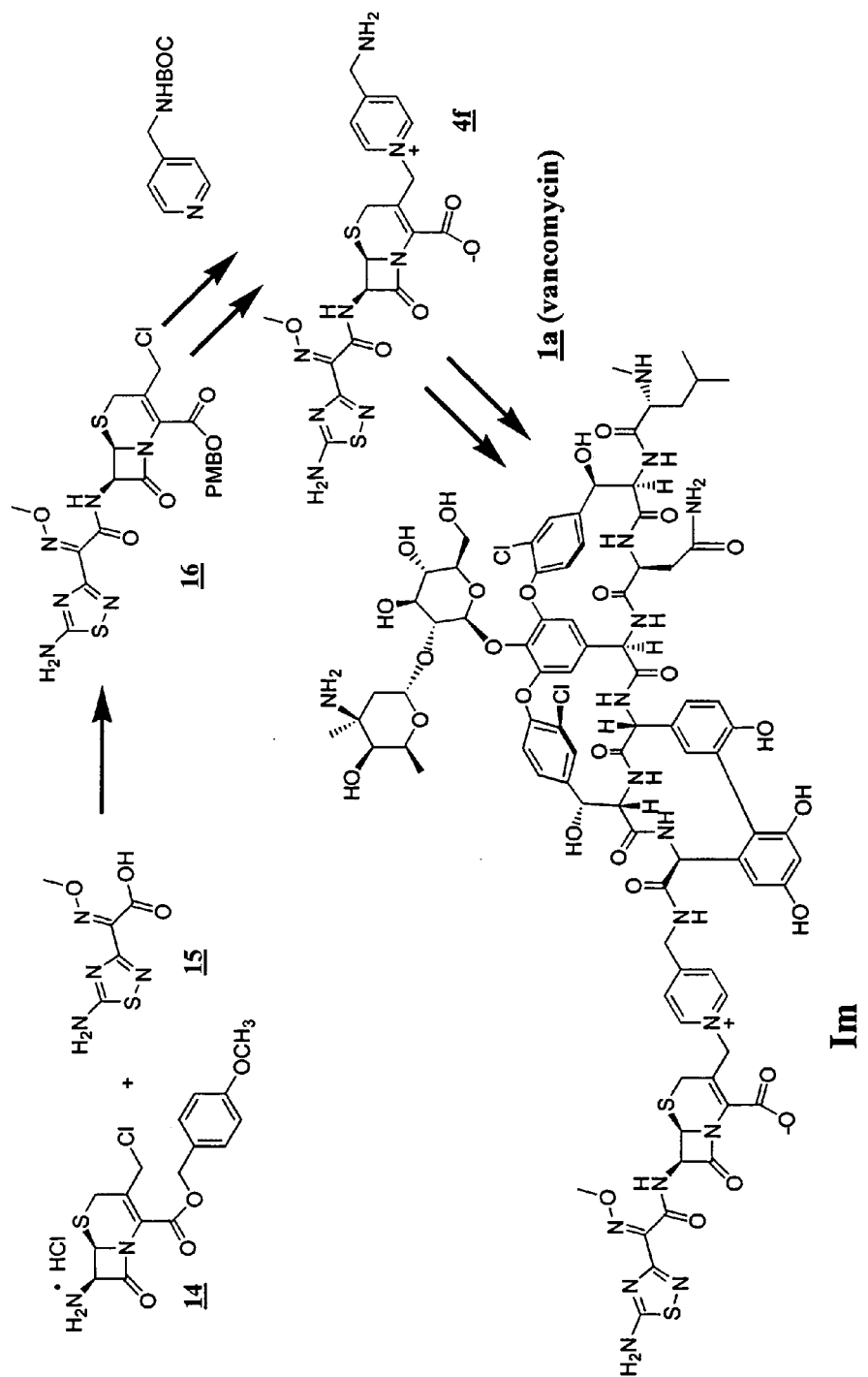
FIGS. 9 and 10 show synthetic schemes for preparing further representative cross-linked glycopeptide-cephalosporin antibiotics.

To a stirred solution of this compound (28.0 g, 60 mmol) in 250 mL of DMF were added 1-(3-dimethylaminopropyl)-3-ethylcarbodiimide (12.7 g, 66 mmol), HOBT (9.0 g, 66 mmol) and 2,4,6-collidine (8.8 mL, 66 mmol). The reaction mixture was cooled to 0° C., and after 5 min 14 (see Example 13; FIG. 9) (24.4 g, 60 mmol) was added. After 3.5 h, the reaction mixture was diluted with ethyl acetate (1200 mL) and washed with 1.0M HCl (250 mL), satd. aqueous sodium bicarbonate (250 mL) and brine (250 mL). The organic layer was dried ($MgSO_4$), filtered and concentrated in vacuo to yield the cephalosporin intermediate 18 (43.2 g, 88%) as an off-white solid, which was used without further purification.

Analytical Data: $^1$H NMR (DMSO-$d_6$, 300 MHz): δ 3.65 (q, 2H), 3.76 (s, 3H), 4.54 (q, 2H), 5.24 (s, 2H), 5.27 (d, 1H), 6.03 (q, 1H), 6.95 (d, 2H), 7.18–7.41 (m, 19H), 9.90 (s, 1H).

Sodium iodide (920 mg, 61 mmol) and N-t-BOC-4-(aminomethyl)pyridine (1.8 g, 86 mmol) were added to a stirred solution of 18 (5 g) in acetone (20 mL) in the dark (foil wrapped flask). The reaction mixture was stirred at room temperature for 2.5 h, then added portionwise to diethyl ether (200 mL) and the resulting solid collected by filtration. A solution of the crude solid (5.9 g) in TFA/DCM (40 mL, 1:1) was stirred at room temperature for 1 h, then added portionwise to diethyl ether (300 mL). The resulting solid was collected by filtration to afford a solid residue which was purified by preparative HPLC to yield the TFA salts of two hydroxyimino stereoisomers (240 mg and 120 mg, respectively) of 4 g (identical to 4b with the exception that $R^9$ is hydrogen), each as a white solid.

Analytical Data:

Major stereoisomer of 4g: $^1$H NMR (DMSO-$d_6$, 300 MHz): δ 3.40 (q, 2H), 4.45 (s, 2H), 5.18 (d, 1H), 5.54 (q, 2H), 5.87 (q, 1H), 7.31 (bs, 2H), 8.18 (d, 2H), 8.71 (bs, 3H), 9.09 (d, 2H), 9.39 (d, 1H), 11.73 (s, 1H); MS m/z obsd. 524.2 [M+H]$^+$.

Minor stereoisomer of 4g: $^1$H NMR (DMSO-$d_6$, 300 MHz): δ 3.50 (q, 2H), 4.45 (s, 2H), 5.19 (d, 1H), 5.58 (q, 2H), 5.83 (q, 1H), 7.27 (bs, 2H), 8.20 (d, 2H), 8.77 (bs, 3H), 8.81 (d, 1H), 9.10 (d, 2H), 12.51 (s, 1H); MS m/z obsd. 524.2 [M+H]$^+$.

A solution of PyBOP (170 mg, 0.33 mmol) and HOAt (44 mg, 0.33 mmol) in DMF (1 mL) was added to a stirred solution of vancomycin hydrochloride (485 mg, 0.33 mmol) in DMSO/DMF (6 mL, 3:1). DIPEA (0.057 mL, 0.33 mmol) was subsequently added, and the reaction mixture was stirred at room temperature for 30 min. TFA (0.026 mL, 0.33 mmol) was added to the reaction mixture, which was then cooled to 0° C., and collidine (0.097 mL, 0.73 mmol) and a solution of 4 (123 mg, 0.16 mmol) in DMF (1 mL) were then added. The reaction mixture was allowed to warm to room temperature over 4 h, then added portionwise to ethyl acetate (50 mL), and the resulting solid was collected by filtration and purified by preparative HPLC to yield the TFA salt of the product In (174 mg, 46%) as a white solid.

Analytical Data: MS m/z obsd. 979.4 [(M-pyridine)/2]$^+$.

Example 15

Determination of Aqueous Solubility

The aqueous solubility of compounds of the invention was determined using the following procedure. A 5 wt. % dextrose buffer solution at pH 2.2 was prepared by adding 1 mL of 1 N hydrochloric acid (Aldrich) to 99 mL of a 5 wt. % aqueous dextrose solution (Baxter). A 1 mg/mL stock solution for calibration standards was then prepared by dissolving 1 mg of the test compound in 1 mL of DMSO. This solution was vortexed for 30 seconds and then sonicated for 10 minutes. The stock solution was then diluted with water to prepare calibration standards having the following concentrations: 50, 125, 250, 375 and 500 µg/mL.

Each test compound (30 mg) was weighed into a Millipore non-sterile, Ultrafree-MC 0.1 µm filter unit (Millipore UFC30VVOO) and a magnetic stir bar was added to each unit. The 5 wt. % dextrose buffer solution (750 µL) was then added to each unit and these mixtures were vortexed for 5 minutes. The filter units were then placed in an Eppendorf tube rack and the tube rack was placed on top of a magnetic stirrer. Each unit was then titrated to pH 3 using 1 N NaOH (VWR) and the resulting solutions centrifuged at 7000 rpm for 5 minutes. Each unit was then diluted 200 fold with 5% dextrose buffer solution and the diluted samples were transferred into auto sampler vials for analysis.

The calibration standards and the test samples were analyzed by reverse-phase HPLC using the following conditions:

Column: Luna 150×4.6 mm; C18; 5µ

Mobile phase: A=5/95, B=95/5, both=MeCN/$H_2O$; 0.1% TFA

Method: 10 m Lido 100 (0–100% B in 6 min)

Injection volume: 20 µL

Wavelength: 214 nm

The solubility of each test sample was calculated by comparing the peak area of the test sample to the calibration curve and multiplying by the dilution factor.

TABLE 1

Solubility (mg/mL) in 5% aqueous dextrose buffer

| Compound No. | Solubility |
| --- | --- |
| Ib | 9.63 |
| Id | 10.0 |
| Ie | 10.0 |
| If | 5.49 |

Example 16

Determination of Minimal Inhibitory Concentrations (MICs)

Minimal inhibitory concentration (MICs) assays were performed using the broth microdilution method set forth in NCCLS guidelines (see, NCCLS. 2000. *Methods for Dilution Antimicrobial Susceptibility Tests for Bacteria That Grow Aerobically*; Approved Standard—Fifth Ed., Vol. 20, No. 2). Bacterial strains were obtained from the American Type Tissue Culture Collection (ATCC), Stanford University Hospital (SU), Kaiser Permanente Regional Laboratory in Berkeley (KPB), Massachusetts General Hospital (MGH), the Centers for Disease Control (CDC), the San Francisco Veterans' Administration Hospital (SFVA) or the University of California San Francisco Hospital (UCSF). Vancomycin-resistant enterococci were phenotyped as Van A or Van B based on their sensitivity to teicoplanin. Some vancomycin-resistant enterococci that had been genotyped as Van A, Van B, Van C1 or Van C2 were also obtained from the Mayo Clinic.

In this assay, cryopreserved bacterial cultures of reference and clinical strains were streaked for isolation on appropriate agar medium (i.e., Trypticase Soy Agar, Trypticase Soy Agar with defibrinated sheep erythrocytes, Brain Heart Infusion Agar, Chocolate Agar). Following incubation to allow formation of colonies, these plates were sealed with Parafilm® and stored refrigerated for up to two weeks. For preparation of assay inocula and to ensure low variability, several colonies from a bacterial isolate cultured on the agar plates were pricked with an inoculating loop and aseptically transferred to Mueller-Hinton Broth (supplemented with divalent cations to required levels based on manufacturer's certification). The broth culture was grown overnight at 35° C., diluted in fresh prewarmed broth and grown to log phase; this is equivalent to a 0.5 MacFarland standard or $1\times10^8$ colony forming units per milliliter (CFU/mL). Not all cell suspensions, due to species variability, contained $1\times10^8$ CFU/mL when turbidity is equivalent to the MacFarland standard, therefore acceptable adjustments (based on NCCLS guidelines) were made in dilutions of different bacterial strains. The inoculum was diluted such that 100 μL of this culture in Mueller-Hinton Broth, supplemented Mueller-Hinton Broth, or *Haemophilus* test medium, when over layered onto a 2-fold serially diluted series of antibiotic concentrations also in 100 μL of corresponding medium, in a 96-well microtiter plate resulted in a starting bacterial concentration of $5\times10^5$ CFU/mL. The plates were then incubated 18–24 hours at 35° C. The MIC was read visually as the lowest concentration well with no bacterial growth. Bacterial growth is defined as more than three pinpoint colonies, a button of precipitated cells larger than 2 mm in diameter, or obvious turbidity.

Strains routinely tested in the initial screen included methicillin-sensitive *Staphylococcus aureus* (MSSA), methicillin-resistant *Staphylococcus aureus* (MRSA), *Staphylococcus aureus* producing penicillinase, methicillin-sensitive *Staphylococcus epidermidis* (MSSE), methicillin-resistant *Staphylococcus epidermidis* (MRSE), vancomycin-sensitive *Enterococcus faecium* (EFMVS), vancomycin-sensitive *Enterococcus faecalis* (EFSVS), vancomycin-resistant *Enterococcus faecium* also resistant to teicoplanin (EFMVR Van A), vancomycin-resistant *Enterococcus faecium* sensitive to teicoplanin (EFMVR Van B), vancomycin-resistant *Enterococcus faecalis* also resistant to teicoplanin (EFSVR Van A), vancomycin-resistant *Enterococcus faecalis* sensitive to teicoplanin (EFSVR Van B), penicillin-sensitive *Streptococcus pneumoniae* (PSSP) and penicillin-resistant *Streptococcus pneumoniae* (PSRP). Because of the inability of PSSP and PSRP to grow well in Mueller-Hinton broth, MICs with those strains were determined using either TS broth supplemented with defibrinated blood or *Haemophilus* test medium.

Test compounds having significant activity against the strains mentioned above were then tested for MIC values in a larger panel of clinical isolates including the species listed above as well as non-speciated coagulase negative *Staphylococcus* both sensitive and resistant to methicillin (MS-CNS and MR-CNS). Additionally, these test compounds were also assayed for MICs against gram-negative microorganisms, such as *Escherichia coli, Pseudomonas aeruginosa, Klebsiella pneumoniae, Enterobacter cloacae, Acinetobacter baumannii, Haemophilus influenzae* and *Moraxella catarrhalis*.

Table 2 shows $MIC_{90}$ data for a compound of this invention against methicillin-resistant *S. aureus* (MRSA) and methicillin-susceptible *S. aureus* (MSSA) as compared to the known antibiotic, vancomycin.

TABLE 2

Minimum Inhibitory Concentrations (MICs), in μg/mL

| Compound | MIC (μg/mL) | |
| --- | --- | --- |
| | MRSA 33591 | MSSA 13709 |
| Ia | 0.13 | <0.1 |
| Ib | <0.1 | <0.1 |
| Ic | <0.1 | <0.1 |
| Id | <0.1 | <0.1 |
| Ie | <0.1 | <0.1 |
| If | <0.1 | <0.1 |
| Ig | 0.78 | <0.1 |
| Ij | 0.78 | <0.1 |
| Ik | 0.45 | <0.1 |
| Im | <0.1 | <0.1 |
| In | <0.1 | <0.1 |
| Vancomycin | 2.0 | 1.0 |

The data in Table 2 demonstrate that compounds of this invention (i.e., Ia, Ib, Ic, Id, Ie, If, Im and In) had surprising and unexpected antibacterial activity against MRSA 33591 compared to either the des-chloro analogs Ig, Ij and Ik or vancomycin; and that compounds of this invention had surprising and unexpected antibacterial activity against MSSA 13709 compared to vancomycin.

Example 17

Time-Kill Assay

This time-kill assay is a method for measuring the rate of bactericidal activity of a test compound. These procedures are similar to those described in V. Lorian, "Antibiotics in Laboratory Medicine", Fourth Edition, Williams and Wilkins (1996), pages 104–105. A rapid time-kill is desirable to quickly prevent bacterial colonization and reduce host tissue damage.

Bacterial inocula were prepared as described in Example 16 for determination of MIC. Bacteria were diluted in prewarmed media in shake flasks and incubated with shaking (200 rpm, 35° C.). At 0, 1, 4, and 24 hours samples were withdrawn from the flasks and bacteria were enumerated by plate counting. Subsequent to the initial sampling, a compound to be assayed was added to the shake flask culture. Plate counts at these intervals previous to and following addition of the compound were expressed graphically in a time-kill curve. Bactericidal activity is defined as a ≧3 log decrease (reduction greater than or equal to 99.9%) in bacterial cell numbers by 24 hours.

In this assay, a compound of formula I, i.e. compound Ib, was bactericidal against MRSA 33591 at a concentration of ≦1.0 μg/mL in 4 hours. By comparison, vancomycin was bactericidal against MRSA 33591 at a concentration of 4 μg/mL in 24 hours.

Example 18

In Vivo Efficacy Studies in Neutropenic Mice

Animals (Male CD-1 mice, 20–30 g) were acquired from Charles Rivers Laboratories (Gilroy, Calif.) and allowed access to food and water ad libitum. Neutropenia was induced via 200 mg/kg intraperitoneal (IP) injection of cyclophosphamide given four and two days prior to the inoculation of bacteria.

The organism used was either a susceptible or resistant strain of clinically relevant Gram-positive pathogens, such as methicillin-susceptible *Staphylococcus aureus* (MSSA 13709) and methicillin-resistant *Staphylococcus aureus* (MRSA 33591). The bacterial inoculum concentration was ~$10^6$ CFU/mL. Animals were lightly anesthetized with isoflurane and 50 mL of the bacterial inoculum was injected into the anterior thigh. One hour after the inoculation, animals were dosed intravenously with vehicle or the appropriate dose of the test compound. At 0 hours and 24 hours post-treatment, the animals were euthanized ($CO_2$ asphyxiation) and the anterior and posterior thigh collected aseptically. The thigh was placed into 10 mL sterile saline and homogenized. Dilutions of the homogenate were plated onto triptic soy agar plates which were incubated overnight. The number of bacterial colonies on a given plate was multiplied by the dilution factor, divided by the thigh weight (in grams) and expressed as log CFU/g. $ED_{50}$ (dose required to produce 50% of the maximum reduction in thigh titre) was estimated for each test compound.

In this assay, a compound of formula I, i.e. compound Ib, had an $ED_{50}$ of <0.1 mg/kg, iv, compared to an $ED_{50}$ of 9 mg/kg, iv, for vancomycin.

While the present invention has been described with reference to specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited herein are incorporated by reference herein in their entirety to the same extent as if they had been individually incorporated by reference.

What is claimed is:

1. A compound of formula I:

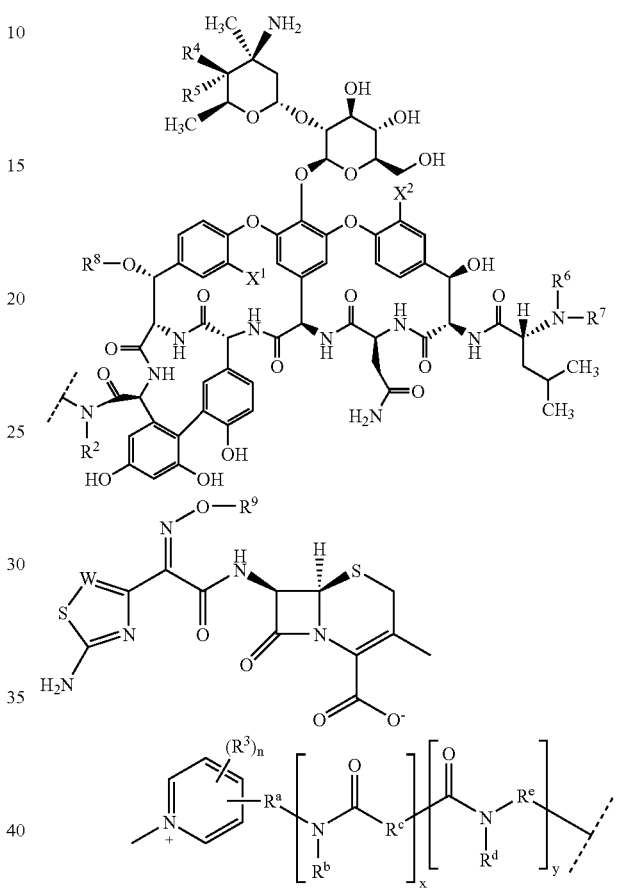

or a pharmaceutically-acceptable salt thereof, wherein:
each of $X^1$ and $X^2$ is independently hydrogen or chloro;
W is selected from N and CCl;
$R^2$ is hydrogen or $C_{1-6}$ alkyl;
one of $R^4$ and $R^5$ is hydroxy and the other is hydrogen;
each of $R^6$ and $R^7$ is independently hydrogen or methyl;
$R^8$ is hydrogen or a group of the formula:

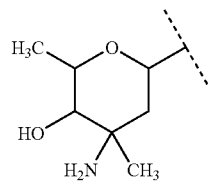

$R^9$ is selected from hydrogen, $C_{1-6}$ alkyl, and $C_{3-6}$ cycloalkyl, where alkyl and cycloalkyl may be substituted with —COOH or 1 to 3 fluorine atoms;
each $R^3$ is independently selected from $C_{1-6}$ alkyl, —OR, halo, —SR, —S(O)R, —S(O)$_2$R, and —S(O)$_2$OR, where each R is independently $C_{1-6}$ alkyl, which may be substituted with COOH or 1 to 3 fluorine atoms;

n is 0, 1, 2 or 3;
x is 0, 1 or 2;
y is 0, 1 or 2;
$R^a$ is —Y—R"—, where
R" is selected from $C_{1-12}$ alkylene, $C_{2-12}$ alkenylene, $C_{2-12}$ alkynylene, $C_{3-6}$ cycloalkylene, $C_{6-10}$ arylene, $C_{2-9}$ heteroarylene, $C_{3-6}$ heterocycle, and combinations thereof, and is optionally substituted with 1 or 2 groups selected from Z, where Z consists of —OR', —SR', —F, —Cl, —N(R')$_2$, —OC(O)R', —C(O)OR', —NHC(O)R', —C(O)N(R')$_2$, —CF$_3$, and —OCF$_3$, and side chains of naturally occurring amino acids, where each R' is independently hydrogen or $C_{1-4}$ alkyl; and R" contains at most 20 non-hydrogen atoms;
Y, which links R" to the pyridinium ring at a meta or para position, is selected from a direct bond, NR', O, S, C(O), NR'C(O), and C(O)NR', precluding direct bonds between heteroatoms in Y and R";
each $R^b$ and $R^d$ is independently selected from the group consisting of hydrogen, $C_{1-6}$ alkyl, $C_{2-6}$ alkenyl, and $C_{2-6}$ alkynyl;
each $R^c$ is independently —Y'—R"—Y'—, where each Y' is independently selected from a direct bond, O, and NR', precluding direct bonds between heteroatoms in Y' and R"; and
each $R^e$ is independently selected from R".

2. The compound of claim 1, wherein $R^9$ is hydrogen or $C_{1-4}$ alkyl.

3. The compound of claim 2, wherein $R^9$ is hydrogen or methyl.

4. The compound of claim 1, wherein W is CCl.

5. The compound of claim 1, wherein W is N.

6. The compound of claim 1, wherein each $R^3$ is independently selected from unsubstituted $C_{1-4}$ alkyl, unsubstituted $C_{1-4}$ alkoxy, fluoro, and chloro.

7. The compound of claim 1, wherein n is 0.

8. The compound of claim 1, wherein x is 1 and y is 0.

9. The compound of claim 8, wherein $R^a$ is —Y—R"—; Y is a direct bond; and R" is $C_{1-6}$ alkylene.

10. The compound of claim 9, wherein $R^c$ is —Y'—R"—Y'—, where each Y' is a direct bond; and R" is $C_{1-12}$ alkylene optionally substituted with a —COOH group.

11. The compound of claim 10, wherein $R^b$ is hydrogen or $C_{1-4}$ alkyl.

12. The compound of claim 1, wherein x is 1 and y is 1.

13. The compound of claim 12, wherein $R^a$ is —Y—R"—; Y is a direct bond; and R" is $C_{1-6}$ alkylene.

14. The compound of claim 13, wherein $R^c$ is —Y'—R"—Y'—, where each Y' is a direct bond; and R" is $C_{1-12}$ alkylene optionally substituted with a —COOH group.

15. The compound of claim 14, wherein $R^e$ is $C_{1-12}$ alkylene.

16. The compound of claim 15, wherein $R^b$ and $R^d$ are independently hydrogen or $C_{1-4}$ alkyl.

17. The compound of claim 1, wherein x is 0 and y is 0.

18. The compound of claim 17, wherein $R^a$ is —Y—R"—; Y is a direct bond; and R" is $C_{1-6}$ alkylene.

19. The compound of claim 1, wherein $R^2$ is hydrogen.

20. A compound of formula II:

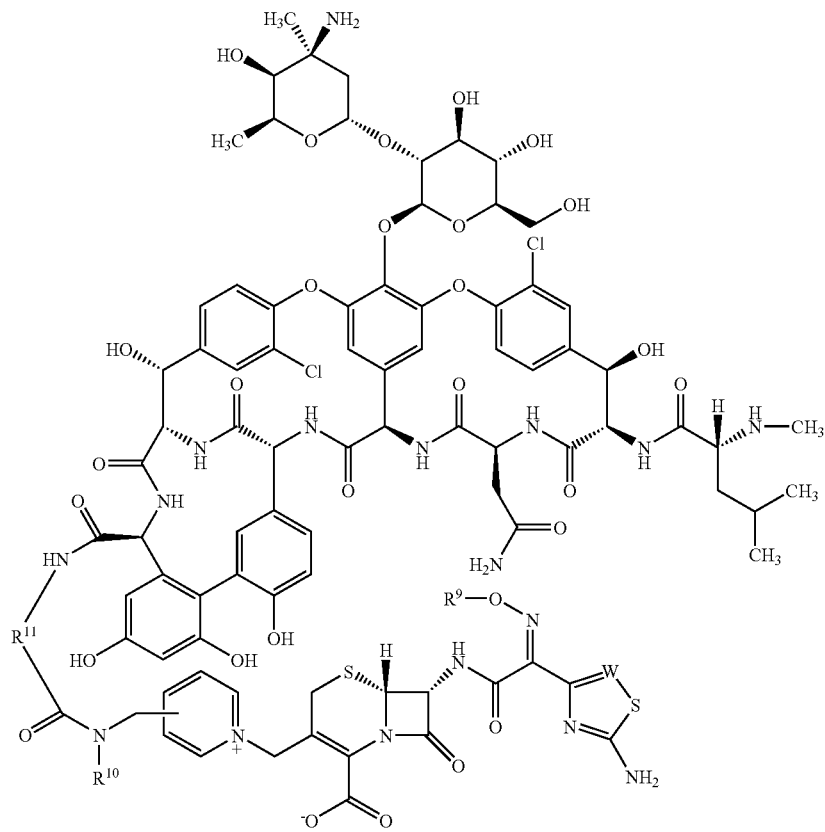

or a pharmaceutically acceptable salt thereof; wherein
W is selected from N and CCl;

$R^9$ is selected from hydrogen, $C_{1-6}$ alkyl, and $C_{3-6}$ cycloalkyl, where alkyl and cycloalkyl may be substituted with —COOH or 1 to 3 fluorine atoms;

the pyridinium ring has meta or para substitution;

$R^{10}$ is hydrogen or $C_{1-6}$ alkyl; and $R^{11}$ is $C_{1-12}$ alkylene.

21. The compound of claim 20, wherein W is CCl.

22. The compound of claim 20, wherein $R^9$ is hydrogen or $C_{1-4}$ alkyl.

23. The compound of claim 22, wherein $R^9$ is hydrogen.

24. The compound of claim 22, wherein $R^9$ is methyl.

25. The compound of claim 20, wherein the pyridinium ring is attached at the para position.

26. The compound of claim 20, wherein $R^{10}$ is hydrogen or $C_{1-4}$ alkyl.

27. The compound of claim 26, wherein $R^{10}$ is hydrogen, methyl or ethyl.

28. The compound of claim 20, wherein $R^{11}$ is $C_{1-10}$ alkylene.

29. The compound of claim 28, wherein $R^{11}$ is —$(CH_2)_2$— or —$(CH_2)_5$—.

30. The compound of claim 20, wherein W is CCl; $R^9$ is methyl; $R^{10}$ is ethyl, $R^{11}$ is —$(CH_2)_2$—; and the pyridinium ring is para substituted.

31. A pharmaceutical composition comprising a pharmaceutically acceptable carrier and a therapeutically effective amount of a compound of any one of claims 1, 20 and 30.

32. A method of inhibiting the growth of bacteria, the method comprising contacting bacteria with a growth-inhibiting amount of a compound of any one of claims 1, 20 and 30.

33. A method of treating a bacterial infection in a mammal, the method comprising administering to a mammal a pharmaceutical composition comprising a pharmaceutically acceptable carrier and a therapeutically effective amount of a compound of any one of claims 1, 20 and 30.

34. A process for preparing a compound of formula I:

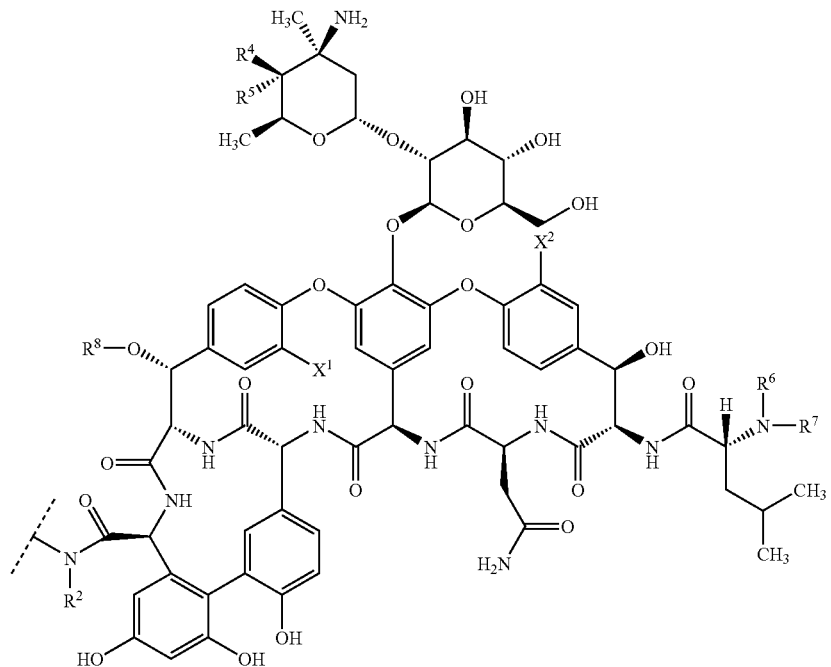

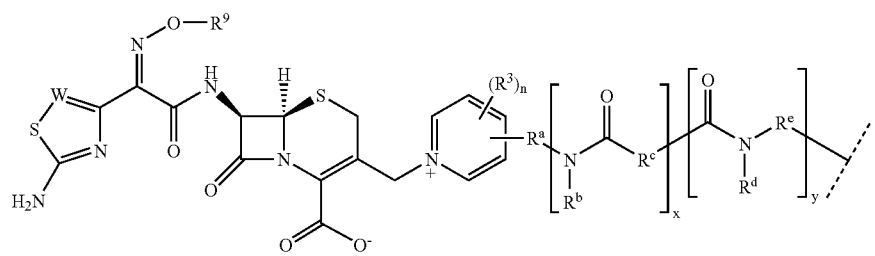

or a salt thereof, wherein:

each of $X^1$ and $X^2$ is independently hydrogen or chloro;

W is selected from N and CCl;

$R^2$ is hydrogen or $C_{1-6}$ alkyl;

one of $R^4$ and $R^5$ is hydroxy and the other is hydrogen;

each of $R^6$ and $R^7$ is independently hydrogen or methyl;

$R^8$ is hydrogen or a group of the formula:

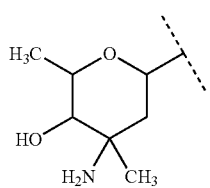

$R^9$ is selected from hydrogen, $C_{1-6}$ alkyl, and $C_{3-6}$ cycloalkyl, where alkyl and cycloalkyl may be substituted with —COOH or 1 to 3 fluorine atoms;

each $R^3$ is independently selected from $C_{1-6}$ alkyl, —OR, halo, —SR, —S(O)R, —S(O)$_2$R, and —S(O)$_2$OR, where each R is independently $C_{1-6}$ alkyl, which may be substituted with COOH or 1 to 3 fluorine atoms;

n is 0, 1, 2 or 3;

x is 0, 1 or 2;

y is 0, 1 or 2;

$R^a$ is —Y—R"—, where

R" is selected from $C_{1-12}$ alkylene, $C_{2-12}$ alkenylene, $C_{2-12}$ alkynylene, $C_{3-6}$ cycloalkylene, $C_{6-10}$ arylene, $C_{2-9}$ heteroarylene, $C_{3-6}$ heterocycle, and combinations thereof, and is optionally substituted with 1 or 2 groups selected from Z, where Z consists of —OR', —SR', —F, —Cl, —N(R')$_2$, —OC(O)R', —C(O)OR', —NHC(O)R', —C(O)N(R')$_2$, —CF$_3$, and —OCF$_3$, and side chains of naturally occurring amino acids, where each R' is independently hydrogen or $C_{1-4}$ alkyl; and R" contains at most 20 non-hydrogen atoms;

Y, which links R" to the pyridinium ring at a meta or para position, is selected from a direct bond, NR', O, S, C(O), NR'(CO), and (CO)NR', precluding direct bonds between heteroatoms in Y and R";

each $R^b$ and $R^d$ is independently selected from the group consisting of hydrogen, $C_{1-6}$ alkyl, $C_{2-6}$ alkenyl, and $C_{2-6}$ alkynyl;

each $R^c$ is independently —Y'—R"—Y'—, where each Y' is independently selected from a direct bond, O, and NR', precluding direct bonds between heteroatoms in Y' and R"; and each $R^e$ is independently selected from R";

wherein the process comprises reacting a compound of formula 1:

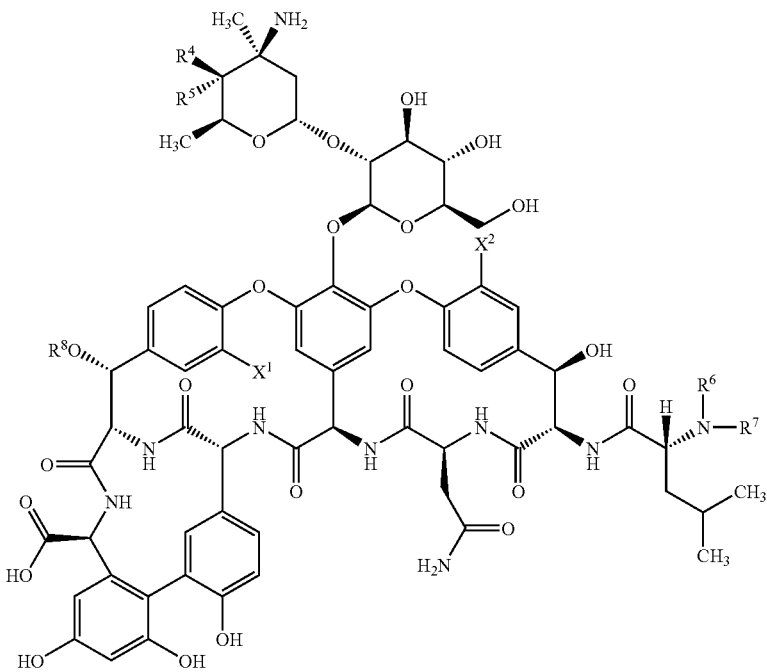

or a salt or activated or protected derivative thereof, with a compound of formula 3 or 4:
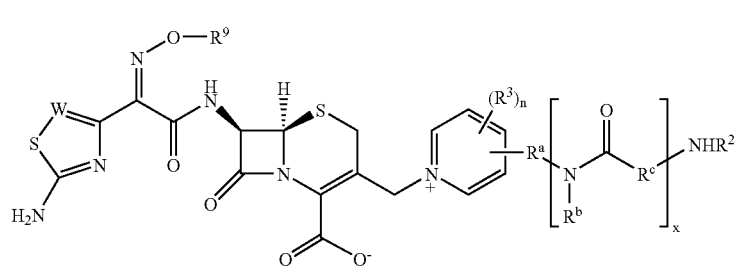
3
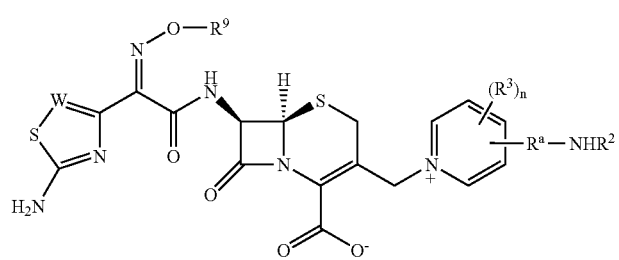
4
or a salt or activated or protected derivative thereof to provide a compound of formula I or a salt thereof.
35. A process for preparing a compound of formula I:
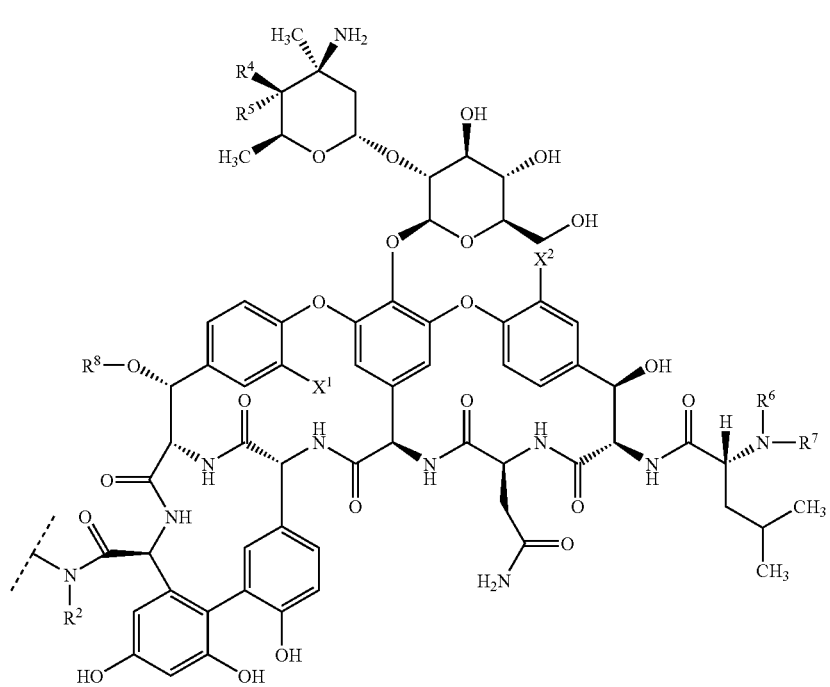
I -continued

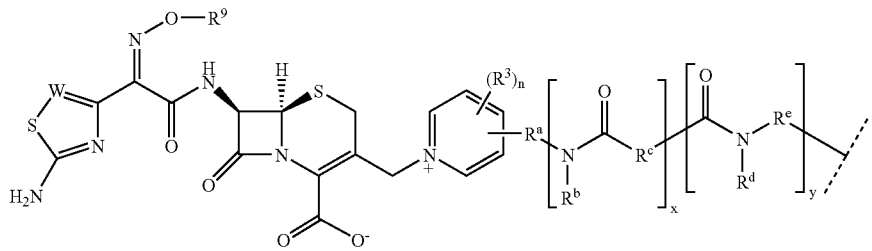

or a salt thereof, wherein:
each of $X^1$ and $X^2$ is independently hydrogen or chloro;
W is selected from N and CCl;
$R^2$ is hydrogen or $C_{1-6}$ alkyl;
one of $R^4$ and $R^5$ is hydroxy and the other is hydrogen;
each of $R^6$ and $R^7$ is independently hydrogen or methyl;
$R^8$ is hydrogen or a group of the formula:

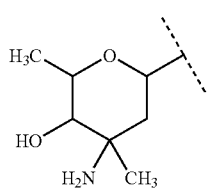

$R^9$ is selected from hydrogen, $C_{1-6}$ alkyl, and $C_{3-6}$ cycloalkyl, where alkyl and cycloalkyl may be substituted with —COOH or 1 to 3 fluorine atoms;
each $R^3$ is independently selected from $C_{1-6}$ alkyl, —OR, halo, —SR, —S(O)R, —S(O)$_2$R, and —S(O)$_2$OR, where each R is independently $C_{1-6}$ alkyl, which may be substituted with COOH or 1 to 3 fluorine atoms;
n is 0, 1, 2 or 3;

x is 0, 1 or 2;
y is 0, 1 or 2;
$R^a$ is —Y—R"—, where

R" is selected from $C_{1-12}$ alkylene, $C_{2-12}$ alkenylene, $C_{2-12}$ alkynylene, $C_{3-6}$ cycloalkylene, $C_{6-10}$ arylene, $C_{2-9}$ heteroarylene, $C_{3-6}$ heterocycle, and combinations thereof, and is optionally substituted with 1 or 2 groups selected from Z, where Z consists of —OR', —SR', —F, —Cl, —N(R')$_2$, —OC(O)R', —C(O)OR', —NHC(O)R', —C(O)N(R')$_2$, —CF$_3$, and —OCF$_3$, and side chains of naturally occurring amino acids, where each R' is independently hydrogen or $C_{1-4}$ alkyl; and R" contains at most 20 non-hydrogen atoms;

Y, which links R" to the pyridinium ring at a meta or para position, is selected from a direct bond, NR', O, S, C(O), NR'(CO), and (CO)NR', precluding direct bonds between heteroatoms in Y and R";

each $R^b$ and $R^d$ is independently selected from the group consisting of hydrogen, $C_{1-6}$ alkyl, $C_{2-6}$ alkenyl, and $C_{2-6}$ alkynyl;

each $R^c$ is independently —Y'—R"—Y'—, where each Y' is independently selected from a direct bond, O, and NR', precluding direct bonds between heteroatoms in Y' and R"; and each $R^e$ is independently selected from R";

wherein the process comprises reacting a compound of formula 5:

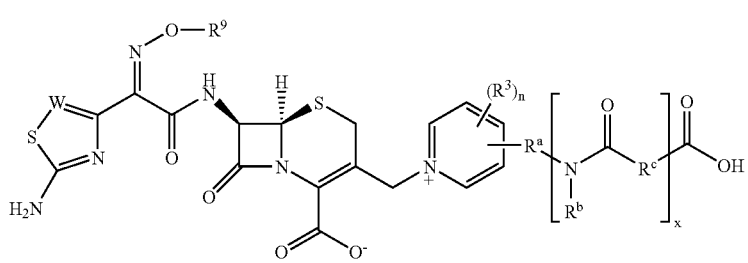

or a salt or activated or protected derivative thereof; with a compound of formula 2:
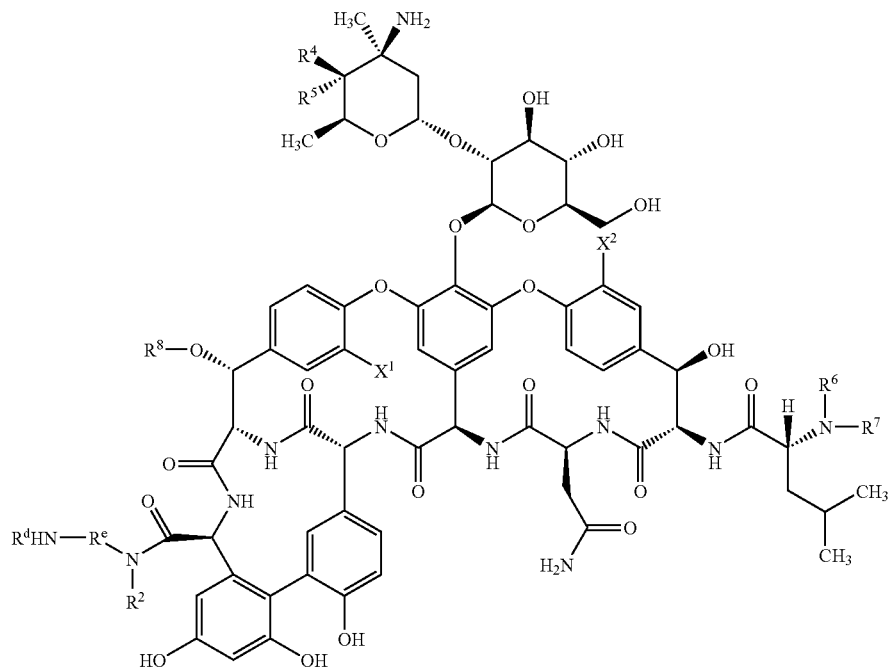
or a salt or activated or protected derivative thereof; to provide a compound of formula I or a salt thereof.
* * * * *